(12) United States Patent
Maschino et al.

(10) Patent No.: US 12,708,571 B2
(45) Date of Patent: Aug. 18, 2026

(54) FORMED FILM LAMINATE FOR ABSORBENT ARTICLES

(71) Applicant: FITESA FILM PRODUCTS LLC, Simpsonville, SC (US)

(72) Inventors: Andrew D. Maschino, Paris, IL (US); Phillip A. Mellor, Simpsonville, SC (US); Jesse B. Schalburg, Terre Haute, IN (US)

(73) Assignee: FITESA FILM PRODUCTS LLC, Simpsonville, SC (US)

( * ) Notice: Subject to any disclaimer, the term of this patent is extended or adjusted under 35 U.S.C. 154(b) by 218 days.

(21) Appl. No.: 18/581,244

(22) Filed: Feb. 19, 2024

(65) Prior Publication Data

US 2024/0245558 A1 Jul. 25, 2024

Related U.S. Application Data

(63) Continuation-in-part of application No. 17/096,335, filed on Nov. 12, 2020, now Pat. No. 11,986,378.

(Continued)

(51) Int. Cl.

*A61F 13/537* (2006.01)
*A61F 13/15* (2006.01)
*A61F 13/534* (2006.01)

(52) U.S. Cl.

CPC .. *A61F 13/53747* (2013.01); *A61F 13/15699* (2013.01); *A61F 13/53713* (2013.01);

(Continued)

(58) Field of Classification Search

CPC .............. A61F 13/5126; A61F 13/5116; A61F 13/53713; A61F 13/53747;

(Continued)

(56) References Cited

U.S. PATENT DOCUMENTS 7,198,836 B2 4/2007 Thomas
2001/0047159 A1 11/2001 Mizutani (Continued)

FOREIGN PATENT DOCUMENTS

CN 1213288 A 4/1999
CN 1705464 A 12/2005

(Continued)

OTHER PUBLICATIONS

Chinese Office Action dated Apr. 20, 2023, for Chinese Patent Application No. 202080086717.6.

(Continued)

*Primary Examiner* — Susan S Su
(74) *Attorney, Agent, or Firm* — KARCESKI IP LAW, PLLC

(57) ABSTRACT

A formed film laminate includes two formed films. Each formed film includes a first side and a second side. The first side includes a plurality of elongated ridges extending from a first land area, a plurality of valleys defined by adjacent elongated ridges and the first land area, and a plurality of primary apertures located at bottoms of the valleys. The second side includes a plurality of apertured protuberances extending from a second land area. Each of the protuberances includes a continuous sidewall extending to a distal end that includes a secondary aperture substantially aligned with a primary aperture. The first and second formed films have a thickness greater than about 0.9 mm under a pressure of 0.071 psi. The first formed film and the second formed film are rotationally offset by an angle greater than 0° and less than or equal to 90°.

14 Claims, 22 Drawing Sheets

Related U.S. Application Data

(60) Provisional application No. 62/976,919, filed on Feb. 14, 2020, provisional application No. 62/935,480, filed on Nov. 14, 2019.

(52) U.S. Cl.
CPC ............... *A61F 2013/15406* (2013.01); *A61F 2013/53445* (2013.01); *A61F 2013/53782* (2013.01)

(58) Field of Classification Search
CPC .......... A61F 2013/51165; A61F 13/514; A61F 13/515; A61F 13/53; A61F 2013/15926; A61F 13/5121; A61F 13/51104
See application file for complete search history.

(56) References Cited

U.S. PATENT DOCUMENTS

| | | | |
|---|---|---|---|
| 2003/0093048 | A1 | 5/2003 | Mcbride |
| 2004/0161586 | A1 | 8/2004 | Cree et al. |
| 2005/0228353 | A1 | 10/2005 | Thomas |
| 2005/0234417 | A1 | 10/2005 | Yoshimasa et al. |
| 2005/0256475 | A1 | 11/2005 | Komatsu et al. |
| 2005/0267429 | A1 | 12/2005 | Cohen |
| 2012/0310197 | A1 | 12/2012 | Thomas |

FOREIGN PATENT DOCUMENTS

| | | | | | |
|---|---|---|---|---|---|
| CN | 203970682 | U | | 12/2014 | |
| CN | 209361113 | U | | 9/2019 | |
| JP | H07501244 | A | | 2/1995 | |
| JP | 2005296480 | A | | 10/2005 | |
| JP | 2006511367 | A | | 4/2006 | |
| JP | 2007167212 | A | * | 7/2007 | ............. A61F 13/15 |
| JP | 2012120584 | A | | 6/2012 | |

OTHER PUBLICATIONS

Chinese Office Action dated Aug. 19, 2022, for Chinese Patent Application No. 202080086717.6.
Chinese Office Action dated Jan. 10, 2023, for Chinese Patent Application No. 202080086717.6.
Indian Office Action dated Sep. 15, 2022, for Indian Patent Application No. 202217027847.
International Preliminary Report on Patentability dated May 17, 2022, for International Patent Application No. PCT/2022/060192.
International Search Report and Written Opinion dated Mar. 11, 2021, for International Patent Application No. PCT/US2020/060192.
Japanese Office Action dated Apr. 25, 2023, for Japanese Patent Application No. 2022-527184.
Japanese Office Action dated Oct. 31, 2023, for Japanese Patent Application No. 2022-527184.
Korean Office Action dated Nov. 9, 2023, for Korean Patent Application No. 10-2022-7019419.

* cited by examiner

FORMED FILM LAMINATE FOR ABSORBENT ARTICLES

CROSS-REFERENCE TO RELATED APPLICATIONS

This U.S. patent application is a Continuation-In-Part that relies for priority on U.S. Non-Provisional patent application Ser. No. 17/096,335, filed on Nov. 12, 2020. This patent application also claims the benefit of priority from U.S. Provisional Patent Application Ser. No. 62/935,480, filed Nov. 14, 2019, and U.S. Provisional Patent Application Ser. No. 62/976,919, filed Feb. 14, 2020. The contents of all of the priority patent applications are hereby incorporated by reference in their entireties.

FIELD

The present invention is directed to a formed film laminate that may be used in absorbent articles, as well as absorbent articles that include the formed film laminate.

BACKGROUND

A variety of well-known absorbent articles are configured to absorb body fluids. Examples of such absorbent articles include, but are not limited to, feminine hygiene products, such as sanitary napkins, baby diapers, adult incontinence products, and bandages. A typical absorbent article is generally constructed with a fluid permeable user-facing topsheet, which may be a three dimensional apertured polymer film or a nonwoven web or a film/nonwoven laminate, an absorbent core and a fluid impermeable garment or outwardly-facing backsheet, which may be a solid polymer film, for example.

A potential problem associated with absorbent articles may be the perceived lack of dryness of the user-facing topsheet of the absorbent article. Generally, the drier the skin feels that is contacting topsheet, the more comfortable the absorbent article. In many instances, surface dryness of the topsheet may be correlated to fluid strikethrough efficiency. If the layer(s) beneath the topsheet are inefficient in fully pulling the fluid out of the topsheet, residual wetness can remain. Moreover, wetness may reoccur and contribute to residual wetness if the fluid is allowed to move from the layer(s) beneath the topsheet and back through the topsheet when the absorbent article is subjected to pressure, which is a typical condition when the article is being worn by a user.

One or more additional layers may be added to the absorbent article in between the topsheet and absorbent core to improve fluid acquisition out of the topsheet and/or fluid distribution across the absorbent core, so that the fluid may be pulled through and out of the topsheet and into the absorbent core more quickly and/or more completely, thus preventing the fluid from moving back through the topsheet. Because the absorbent core is generally rectangular in shape, it is desirable to move the fluid preferentially across the longer dimension rather that the shorter dimension. Such preferential movement may also reduce or prevent leakage out the side of the absorbent article, which is desirable.

Still further, there is a general desire for the construction of a topsheet that provides a high thickness, or "loft." A higher loft material has an aesthetically pleasing, visual appearance, because a thicker material looks to be more absorbent than a thinner material. Moreover, a higher loft material has an improved tactile response, because the material feels more substantial to the user.

However, as a general rule, materials with a higher loft often tend to perform less favorably as topsheets and fluid distribution materials than lower loft materials. One reason for this is that a thicker material presents a larger barrier to the passage of fluids therethrough. As a result, thicker materials tend to retain surface moisture after being exposed to a fluid. This increases the feeling of "wetness" associated with such materials. In addition, thicker materials typically have a longer strikethrough time, because the increased thickness of the material presents additional barriers to the passage of fluids therethrough. Again, this contributes to a material with a higher perceived lack of dryness.

While thicker materials for topsheets and fluid distribution materials are typically overlooked due to their decreased performance, there remains a considerable desire for high loft materials for topsheets and fluid distribution materials, among others.

In addition, materials that have a high loft also tend to be expensive to manufacture. For this additional reason, high loft materials typically are disfavored as materials for topsheets and fluid distribution materials.

SUMMARY

According to an aspect of the invention, a formed film laminate includes a first formed film and a second formed film. The first formed film includes a first side with a plurality of protrusions in the form of elongated ridges having peaks extending from a first land area of the first side and oriented in a first direction, a plurality of valleys defined by adjacent protrusions and the first land area and oriented in the first direction, and a plurality of primary apertures located at bottoms of the valleys. The first formed film also includes a second side opposite the first side. The second side includes a plurality of apertured protuberances, each of the apertured protuberances comprising a continuous sidewall extending from a second land area of the second side to a distal end comprising a secondary aperture, wherein each secondary aperture is substantially aligned with a primary aperture. The first formed film has a thickness greater than about 0.9 mm under a pressure of 0.071 psi, and a thickness greater than about 0.3 mm under a pressure of 0.6 psi, the plurality of protrusions excludes the plurality of primary apertures and the plurality of apertured protuberances, the plurality of protrusions are narrower than the plurality of valleys, and the peaks are spaced from the first land area by a first distance that is uniform from a first end to a second end in the first direction. The second formed film has the same construction as the first formed film. The second formed film includes a first side with a plurality of protrusions in the form of elongated ridges having peaks extending from a first land area of the first side and oriented in a first direction, a plurality of valleys defined by adjacent protrusions and the first land area and oriented in the first direction, and a plurality of primary apertures located at bottoms of the valleys. The second formed film also includes a second side opposite the first side, the second side having a plurality of apertured protuberances, each of the apertured protuberances comprising a continuous sidewall extending from a second land area of the second side to a distal end comprising a secondary aperture, wherein each secondary aperture is substantially aligned with a primary aperture. The second formed film has a thickness greater than about 0.9 mm under a pressure of 0.071 psi, and a thickness greater than about 0.3 mm under a pressure of 0.6 psi, the plurality of protrusions excludes the plurality of primary apertures and the plurality of apertured protuberances, the plurality of protrusions are narrower than the plurality of valleys, and the peaks are spaced from the first land area by a first distance that is uniform from a first end to a second end in the first direction. The first formed film and the second formed film are rotationally offset by an angle greater than 0° and less than or equal to 90°.

In one contemplated embodiment, the first formed film in the formed film laminate has a basis weight between about 14 gsm and about 45 gsm.

In another contemplated embodiment, the second formed film in the formed film laminate has a basis weight between about 14 gsm and about 45 gsm.

It is contemplated that the plurality of apertured protuberances in both the first formed film and the second formed film are arranged in a pattern having about 5 to about 45 apertured protuberances per linear inch in the first direction.

It is also contemplated that the plurality of apertured protuberances in the first formed film and the second formed film are spaced from the second land area by a second distance. Here, the first distance is greater than the second distance.

Still further, for the formed film laminate, it is contemplated that the primary apertures include more than one primary aperture between adjacent peaks in a second direction orthogonal to the first direction.

The formed film laminate also may include at least one recessed region in at least one of the elongated ridges.

In another embodiment, the formed film laminate may include at least one unapertured pocket disposed thereon.

The present invention also encompasses an absorbent article that includes a topsheet configured to contact skin of a user of the absorbent article, a backsheet configured to contact a garment of the user of the absorbent article, an absorbent core in between the topsheet and the backsheet and a fluid distribution material in between the topsheet and the absorbent core, at least one of the topsheet and the fluid distribution material being constructed as a formed film laminate.

For the absorbent article it is contemplated that the topsheet is directly bonded to the fluid distribution material.

In one embodiment, the topsheet is vacuum laminated to the fluid distribution material.

The topsheet may comprise the formed film laminate in one embodiment of the absorbent article.

The fluid distribution material may comprise the formed film laminate in another embodiment of the present invention.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

DETAILED DESCRIPTION

Figure 1:
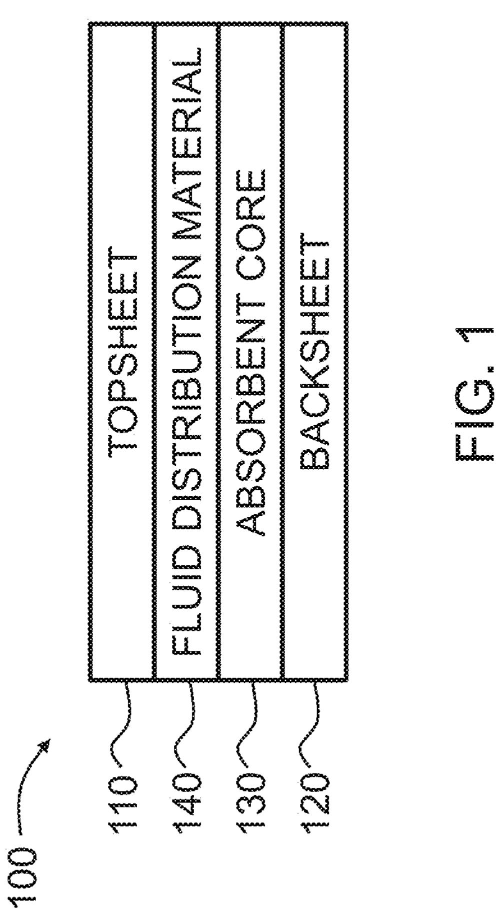
FIG. 1 is a schematic representation of an absorbent article in accordance with embodiments of the invention.

As used herein, the expression "absorbent articles" denote articles that absorb and contain body fluids and other body exudates. More specifically, an absorbent article/absorptive device includes garments that are placed against or in proximity to the body of a wearer to absorb and contain the various exudates discharged from a body. Non-limiting examples of absorbent articles include, but are not limited to feminine hygiene products, baby diapers, adult incontinence products, and bandages.

Throughout this description, the term "web" refers to a material capable of being wound into a roll. Webs can be film webs, nonwoven webs, laminate webs, apertured laminate webs, etc. The face of a web refers to one of its two dimensional surfaces, as opposed to one of its edges.

The term "film" or "polymer film" in this description refers to a web made by extruding a molten curtain or sheet of thermoplastic polymeric material by a cast or blown extrusion process and then cooling the sheet to form a solid polymeric web. Films can be monolayer films, coextruded films, coated films, and/or composite films.

Throughout this description, the expression "apertured films" denote films that have a plurality of apertures that extend from a first surface of the film to a second, opposing surface of the film.

A "two-dimensional apertured film" is a film in which no three-dimensional structure exists in the apertures, which then connect the second surface of a flat film to the first surface of the film.

A "formed film" or a "three-dimensional film" is a film with protuberances or protrusions extending from at least one side thereof, and an "apertured formed film" or a "three-dimensional apertured film" is a film in which a three-dimensional structure exists in the apertures (e.g., the apertures have a depth that is thicker than the thickness of the film), or the protuberances or protrusions or extended cells have apertures therethrough.

The term "protuberance" as used herein refers to a three-dimensional member comprising an apertured base portion located in the plane of the first surface of the film and a sidewall portion extending generally in the direction away from the first surface of the film. Each base portion has an associated sidewall portion. Sidewall portions terminate in "distal ends" located in the plane spaced from the first surface of the film. The distal ends of the protuberances may be apertured or unapertured.

"Apertured protuberance" as used herein refers to a protuberance that has an aperture at its base portion or proximal end in the plane of the first surface, as well as its distal or protubered end. The apertures in the base portions of the protuberances, also called "primary apertures," may be in the shape of polygons, for example squares, hexagons, pentagons, ellipses, circles, ovals, or slots, in a regulated or random pattern. In an embodiment, the apertures may be in the shape of a boat, as described in, for example, U.S. Pat. No. 7,198,836, which is incorporated herein by reference.

The apertured distal or protubered ends are called "secondary apertures," and may be in the shape of polygons, e.g., squares, hexagons, pentagons, ellipses, circles, ovals, slots, or boats. The sidewall portion of the apertured protuberance extends from the primary aperture to the secondary aperture.

The term "forming structure" or "screen" as used herein refers to a three-dimensional molding apparatus that comprises indentations and/or raised portions or protrusions used to form protuberances, and/or apertures in films. In an embodiment, forming structures comprise tubular members, having a width and a diameter. In alternative embodiments, forming structures may comprise belts having a width and a length. The transverse direction is the direction parallel to the width of the forming structure. The machine direction is the direction parallel to the direction of rotation of the forming structure, and is perpendicular to the transverse direction.

Various embodiments of the present invention will now be described. The discussion of any one embodiment is not intended to limit the scope of the present invention. To the contrary, aspects of the embodiments are intended to emphasize the breadth of the invention, whether encompassed by the claims or not. Furthermore, any and all variations of the embodiments, now known or developed in the future, also are intended to fall within the scope of the invention.

FIG. 1 schematically illustrates an absorbent article 100 in accordance with embodiments of the invention. As illustrated, the absorbent article 100 includes a topsheet 110, a backsheet 120, and an absorbent core 130 positioned in between the topsheet 110 and the backsheet 120. The absorbent article 100 also includes a fluid distribution material 140 positioned in between the topsheet 110 and the absorbent core 130.

The topsheet 110, which may be in the form of a two-dimensional or three-dimensional apertured film, a nonwoven web, or a laminate of an apertured film and a nonwoven web, is permeable to fluids and is configured to face the user wearing the absorbent article 100 and contact the user's skin. The topsheet 110 may be bonded directly to the fluid distribution material 140 by any known means in the art, including by not limited to adhesive bonding, thermal bonding, thermal point bonding, sonic bonding, and vacuum formed lamination (as described below), prior to assembly of the absorbent article 100.

The topsheet 110 receives insults of fluid from the user, and the fluid passes through the topsheet 110 to the fluid distribution material 140. The fluid distribution material 140 is also permeable and is configured to receive the fluid from the topsheet 110 and distribute the fluid to the absorbent core 130. The absorbent core 130, which includes absorbent materials, receives the fluid from the fluid distribution material 140 and stores the fluid until the absorbent article 100 is discarded. The backsheet 120, which is impermeable to liquid and may be in the form of a polymer film or laminate of a polymer film and nonwoven web, prevents liquid and other body exudates from leaking out of the bottom side of the absorbent core 130. The backsheet 120 may be breathable so that air, but not liquid, may pass through.

Figures 2A, 2B:
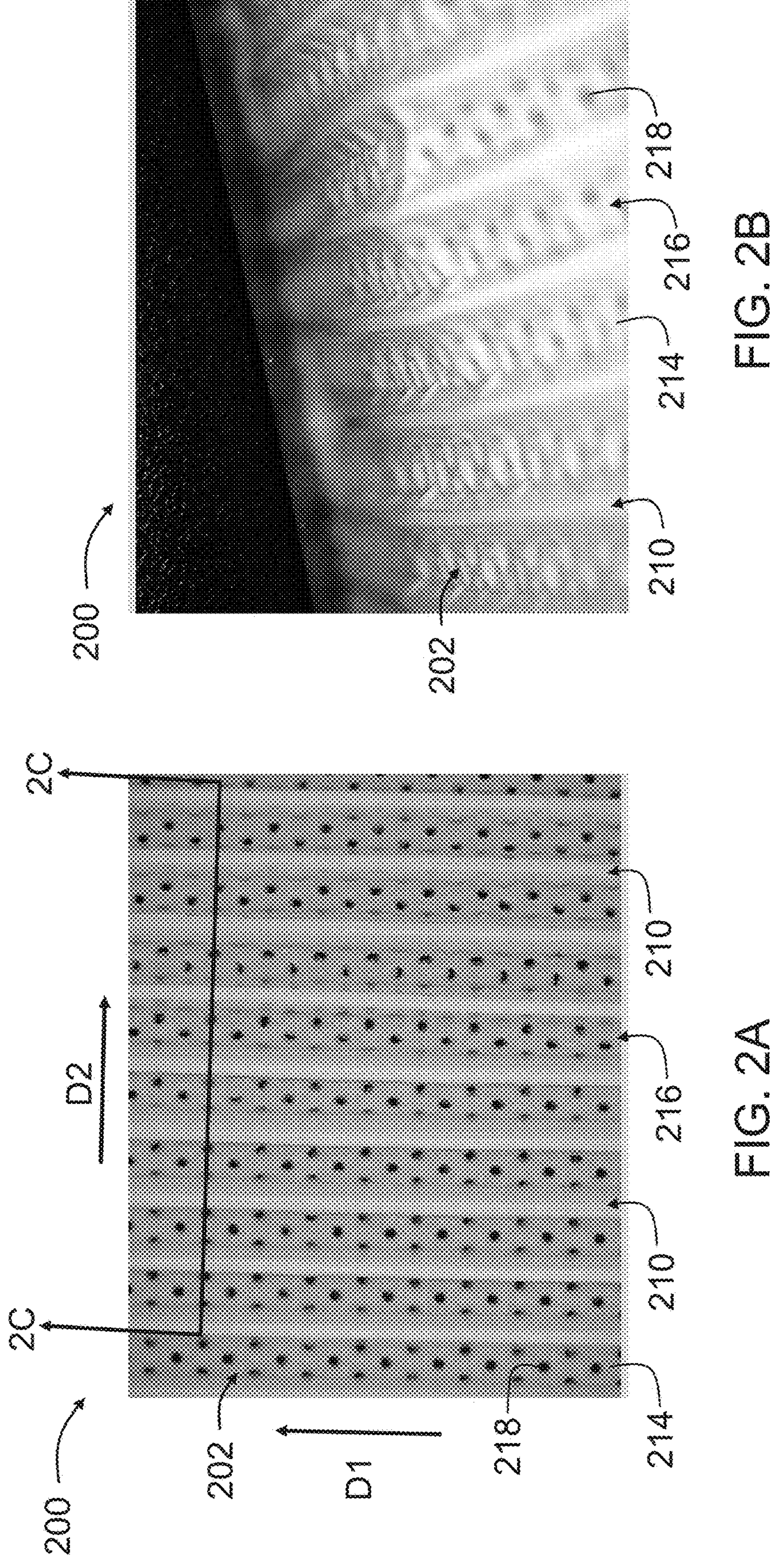
FIG. 2A is a photograph of a top view (user facing side) of an embodiment of a formed film that may be used as a fluid distribution material of the absorbent article of FIG. 1.
FIG. 2B is a photograph of a top perspective view of the formed film of FIG. 2A.
Figure 2C:
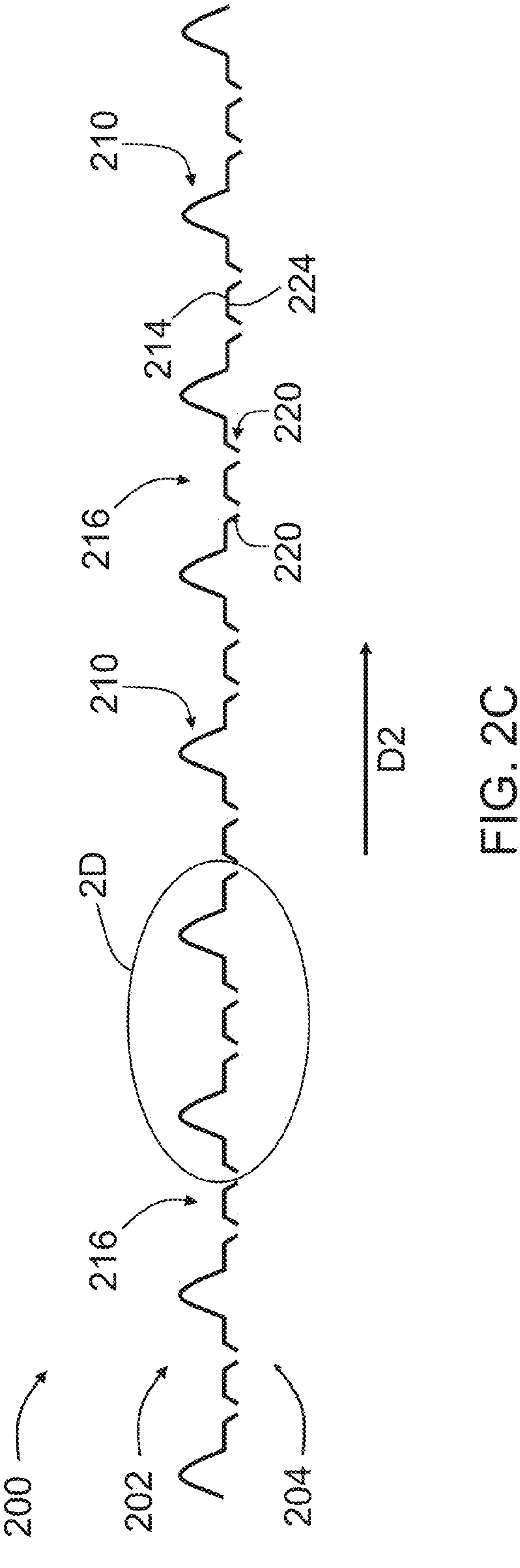
FIG. 2C is a schematic cross-sectional view of the formed film of FIG. 2A taken along line 2C-2C of FIG. 2A.
Figure 2D:
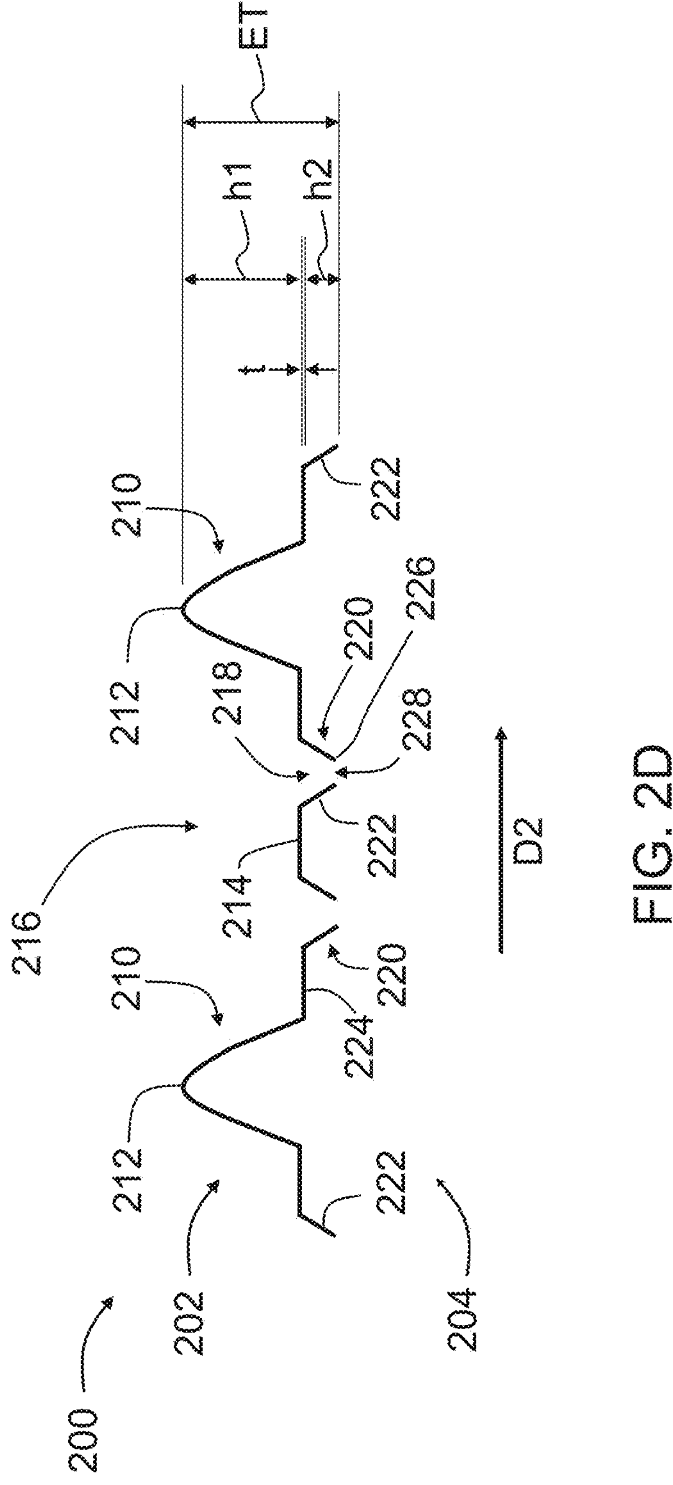
FIG. 2D is an enlarged schematic cross-sectional view of 2D in FIG. 2C.

FIG. 2A is a photograph of a top portion of a formed film 200 (user facing side) according to an embodiment of the invention, which may be used as the fluid distribution material 140 of FIG. 1, and FIG. 2B is a top perspective view of the formed film of FIG. 2A. FIG. 2C is a schematic cross-sectional view of the formed film 200 taken along line 2C-2C in FIG. 2A, and FIG. 2D is an enlarged view of a portion of the film circled as 2D in FIG. 2C. As illustrated, the formed film 200 includes a first side 202, which in an embodiment is configured to face the topsheet 110 of the absorbent article 100, and a second side 204, which in an embodiment is configured to face the absorbent core 130 of the absorbent article 100. In an embodiment, the first side 202 of the formed film 200 may be oriented to face the absorbent core 130, and the second side 204 of the formed film 200 may be oriented to face the topsheet 110.

The first side 202 includes a plurality of protrusions in the form of elongated ridges 210 that are oriented in a first direction D1 of the formed film 200 and have peaks 212 that are spaced from a first land area 214 of the first side 202 by a distance h1. The first side 202 also includes a plurality of valleys 216 defined by adjacent elongated ridges 210 and the first land area 214. The valleys 216 alternate with the elongated ridges 210 in a second direction D2, orthogonal to the first direction D1, and are oriented in the first direction D1. The first side 202 also includes a plurality of primary apertures 218 located at bottoms of the valleys 216.

The second side 204 of the formed film 200 includes a plurality of apertured protuberances 220. Each apertured protuberance 220 has a continuous side wall 222 that extends away from a second land area 224 to a distal end 226. The distal end 226 has a secondary aperture 228 that is substantially aligned with a corresponding primary aperture 218 of the first side 202. The distal ends 226 are spaced from the second land area 224 by a distance h2. The thickness ET of the formed film 200 is the sum of the nominal thickness of the film t between the first and second land areas 214, 224, and the height h1 of the elongated ridges 210, and the height h2 of the apertured protuberances 220.

In an embodiment, the apertured protuberances 220 may be arranged in a pattern having about 5 to about 45 protuberances per linear inch or "mesh," i.e., about 5 mesh to about 45 mesh in at least one direction. The pattern may be a hexagonal pattern, a square pattern, a staggered pattern, or any other type of pattern or design.

The polymer of the formed film 200 may include one or more polyolefins, including but not limited to polyethylene, ultra-low density polyethylene, low density polyethylene, linear low density polyethylene, linear medium density polyethylene, high density polyethylene, polypropylene, ethylene-vinyl acetates, metallocene, as well as other polymers, such as bio-based polymers that are produced from plants, including but not limited to sugarcane, or polylactic acid ("PLA"). Other polymers include, but are not limited to, elastomeric polymers, including but not limited to polypropylene based elastomers, ethylene based elastomers, copolyester based elastomers, olefin block copolymers, styrenic block copolymers and the like, or combinations thereof. Additives, such as surfactants, fillers, colorants, opacifying agents and/or other additives known in the art may also be used in the formed film 200.

In an embodiment, the formed film 200 has a basis weight between about 14 gsm and about 40 gsm. In an embodiment, the formed film has a basis weight between about 20 and about 35 gsm. It is also contemplated that the formed film 200 has a basis weight between about 14 gsm and about 45 gsm in some embodiments.

Figure 3:
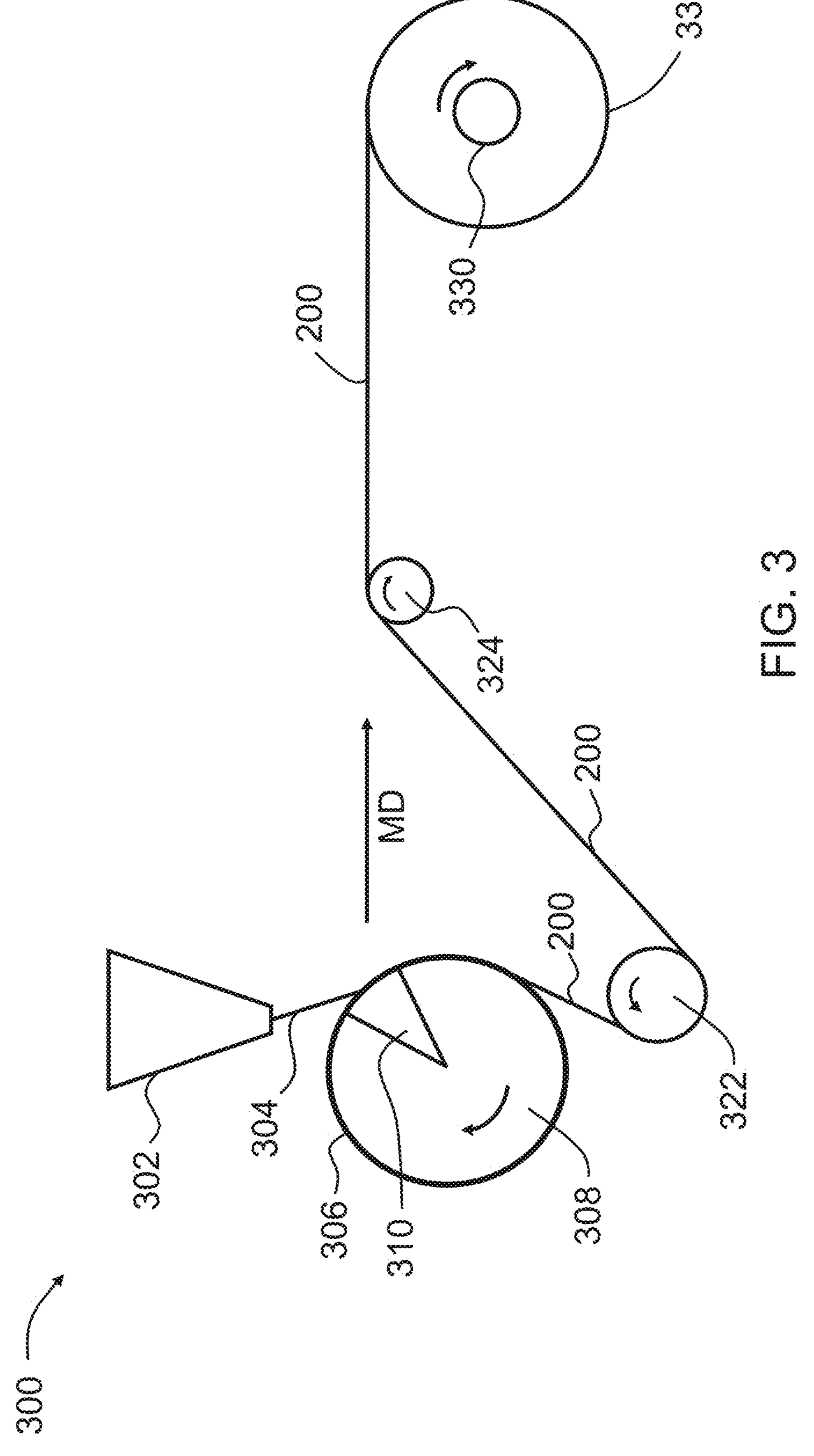
FIG. 3 is a schematic representation of an apparatus for manufacturing the film of FIGS. 2A-2D in accordance with embodiments of the invention.

FIG. 3 schematically illustrates an apparatus 300 that may be used to manufacture the formed film 200 of embodiments of the invention described herein. As illustrated, an extrusion die 302 extrudes a polymer melt curtain 304 onto a forming structure 306 that rotates about a cylinder 308 that has a vacuum slot 310 through which a vacuum is pulled. The forming structure 306 includes a plurality of apertures and a plurality of protrusions extending from an outer surface thereof. The polymer melt curtain 304 may include, for example, one or more polyolefin materials and a surfactant, as well as one or more additives, such as a colorant.

As the polymer web (which solidifies to form, for example, the formed film 200 of FIGS. 2A and 2B) is apertured, air flow is initiated through the apertured protuberances 220 which cools and solidifies the apertured protuberances 220. At the same time, the protrusions on the forming structure 306 shape the polymer web to form the elongated ridges 210. In an embodiment, the protrusions on the forming structure 306 that formed the elongated ridges 210 may be oriented in a machine direction MD. In an embodiment, the protrusions on the forming structure 306 that formed the elongated ridges 210 may be oriented in a cross direction orthogonal to the machine direction MD. The polymer web is also cooled by the forming structure 306. The resulting vacuum formed film 200 is pulled off of forming structure 306 by a peel roller 322 and travels to one or more subsequent rollers 324 until it may be wound by a winder 330 into a roll 332. Additional rollers and/or other pieces of equipment may be used in the apparatus 300. The illustrated embodiment is not intended to be limiting in any way.

EXAMPLES

Comparative: A secondary topsheet ("STS") material, which was positioned between the topsheet and absorbent core and in the form of a spunlace nonwoven material having a basis weight of 50 grams per square meter (gsm), was removed from an ALWAYS® Ultra Thin Feminine Hygiene Pad (Size 2) manufactured by The Procter & Gamble Company of Cincinnati, Ohio and used as a prior art Comparative Example ("Comparative STS").

Example 1: A formed film 200 having the structure illustrated in FIGS. 2A-2D and basis weight of 34 grams per square meter (gsm) was made on the apparatus 300 of FIG. 3 and used as Example 1.

Example 2: A formed film 200 having the structure illustrated in FIGS. 2A-2D and basis weight of 26 grams per square meter (gsm) was made on the apparatus 300 of FIG. 3 and used as Example 2.

Figure 4:
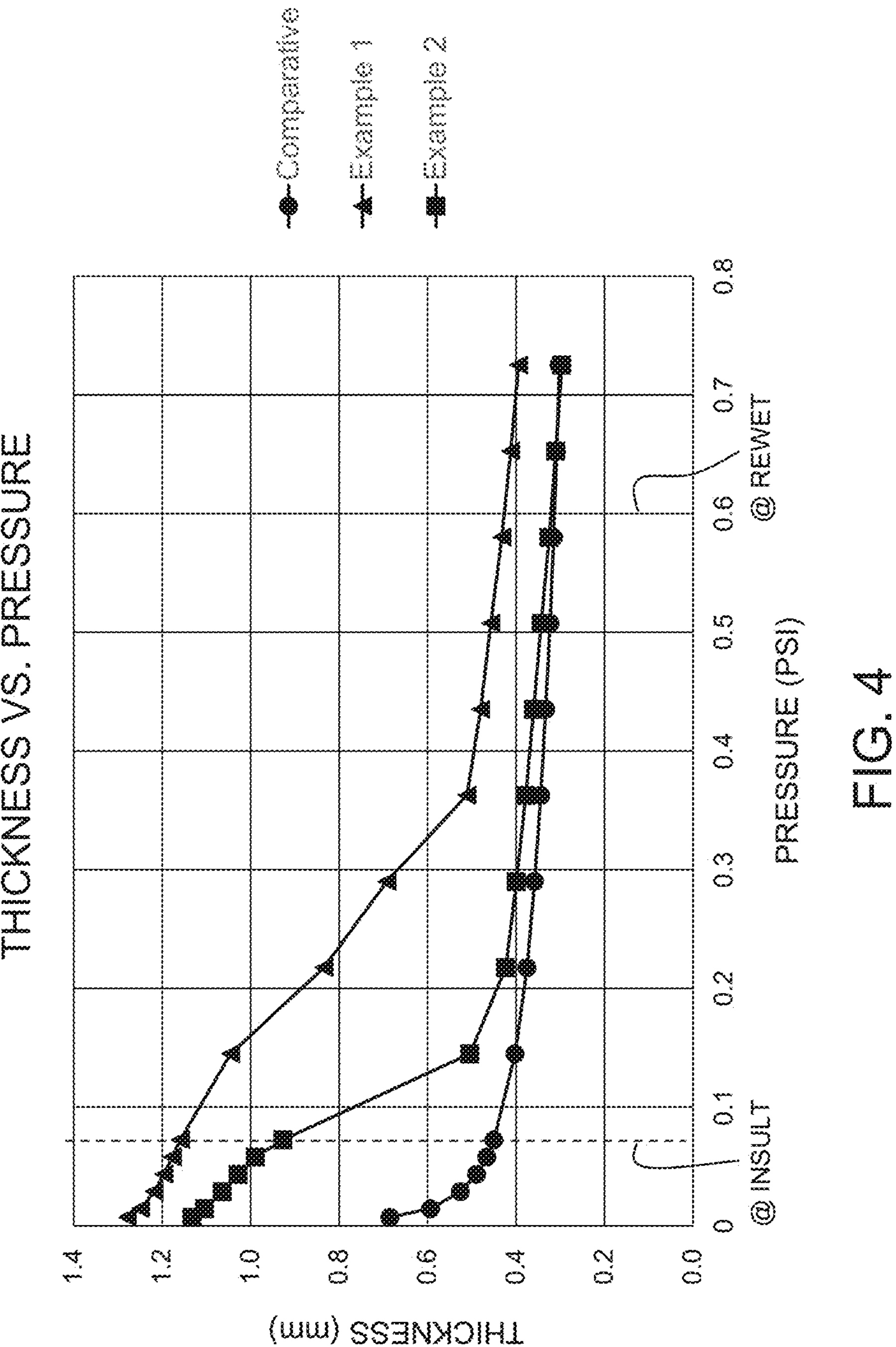
FIG. 4 is a plot illustrating thicknesses of the formed film according to embodiments of the invention, as well as a prior art comparative fluid distribution material as a function of applied pressure.

The materials of the Comparative STS, Example 1 and Example 2 were measured for thickness (compression resistance) under pressures ranging from 0.00725 psi to 0.725 psi using a Vantage$^{NX}$ universal testing machine with a compression fixture by Thwing-Albert Instrument Company. The opening distance between two plates within the instrument was set to 1.27 cm (0.5 inch). Each sample was placed on a lower plate in the instrument and an upper plate was manually lowered to a position just above, but not touching, the sample before the test was started. Three samples for each material were measured and the results were averaged. The results of the testing are illustrated in FIG. 4. The Comparative STS had a lower initial thickness, and all three examples had their thicknesses decrease as the applied pressure was increased, as expected. Example 2 exhibited similar thicknesses as the Comparative STS at pressures above 0.2 psi, and Example 1 exhibited greater thicknesses at all pressures.

In order to test performance of the formed film 200 when used as a fluid distribution material 140 in an absorbent article 100, specifically in a feminine hygiene pad, the STS materials of several ALWAYS® Ultra Thin Feminine Hygiene Pads (size 2) manufactured by The Procter & Gamble Company of Cincinnati, Ohio were removed and replaced with the formed films of Examples 1 and 2 with the distal ends 226 of the apertured protuberances 220 contacting the absorbent core and the peaks 212 of the plurality of elongated ridges 210 contacting the topsheet. The first direction D1 of the formed film 200 was oriented parallel to the length (longer dimension) of the pad so that the plurality of elongated ridges 210 were oriented parallel to the length of the pad. In addition, Comparative Example A was the as-manufactured ALWAYS® Ultra Thin Feminine Hygiene Pad (size 2), and Comparative Example B was the as-manufactured ALWAYS® Ultra Thin Feminine Hygiene Pad (size 2) after the STS material was removed and placed back into the pad in the same manner that was done with Examples 1 and 2.

Examples 1 and 2, and Comparative Examples A and B, described above, were tested for performance characteristics, including multiple strikethrough times and rewet values. For each example, three pads were subjected to three insults of 4 milliliters (ml) of a synthetic blood having a viscosity of 11.1 centipoise (cP), and rewet values were measured after each insult. Specifically, each pad was placed on a flat table top, a 500 g strikethrough plate made from clear plastic with a hole in the center, which resulted in an applied pressure of about 0.071 psi, was placed on top of the topsheet of each pad so that the hole in the plate was centered on the topsheet, and a pump was started to deliver the 4 ml insult in 6 seconds. A stopwatch was started at the same time the pump was started and stopped when the insult liquid in the plate hole was observed to be absorbed by the pad. The recorded time was the first insult strikethrough time in seconds.

The strikethrough plate was removed, five sheets of pre-weighed pickup paper were placed over the insult area and a 4.8 lb. weight, which resulted an applied pressure of 0.6 psi, was placed on top of the sheets of paper for two minutes. After the two minutes, the weight and the five sheets of paper were removed, a picture was taken of the pad, and the five sheets of papers were weighed. The difference between the weight of the "wet" paper and the initial "dry" paper was the measured rewet value in grams. The procedure was repeated for a second insult and a third insult on the same pad.

Figure 5C:
FIG. 5C is a photograph of the prior art absorbent article of FIG. 5B after a third insult of synthetic blood.
Figure 6C:
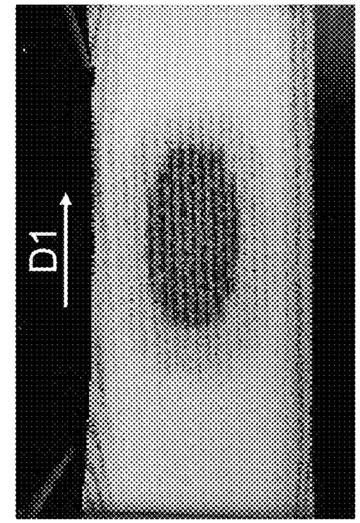
FIG. 6C is a photograph of the absorbent article of FIG. 6B after a third insult of synthetic blood.
Figure 5B:
FIG. 5B is a photograph of the prior art absorbent article of FIG. 5A after a second insult of synthetic blood.
Figure 6B:
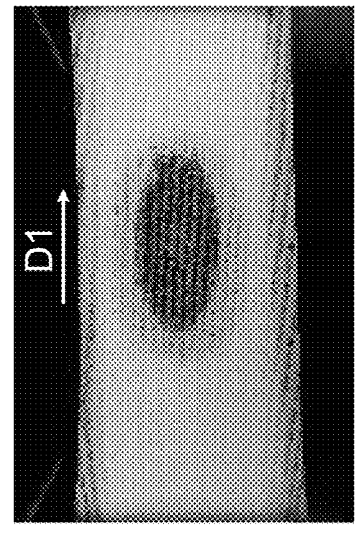
FIG. 6B is a photograph of the absorbent article of FIG. 6A after a second insult of synthetic blood.
Figure 5A:
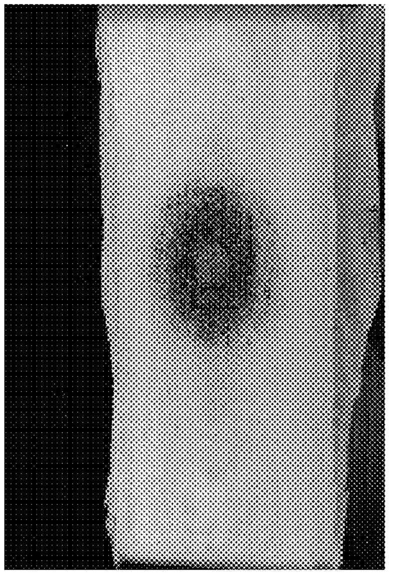
FIG. 5A is a photograph of a prior art absorbent article after a first insult of synthetic blood.
Figure 6A:
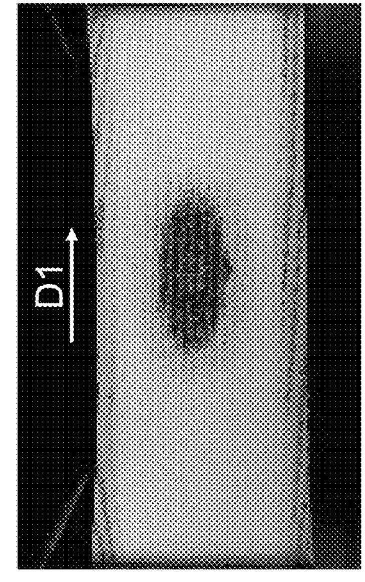
FIG. 6A is a photograph of an absorbent article with a formed film used as a fluid distribution material according to an embodiment of the invention after a first insult of synthetic blood.

FIGS. 5A-5C illustrate the Comparative Example A pads after the first, second, and third insults, respectively, while FIGS. 6A-C illustrate the Example 1 pads after the first, second, and third insults, respectively. As illustrated, the Example 1 pads had stains that were more elongated than the stains of the Comparative Example A stains, which indicates that the structure provided by the formed film 200 helped direct the insult along the length of the pad. Such direction flow may help prevent undesirable side leakages that may be experienced by the user.

Figure 7:
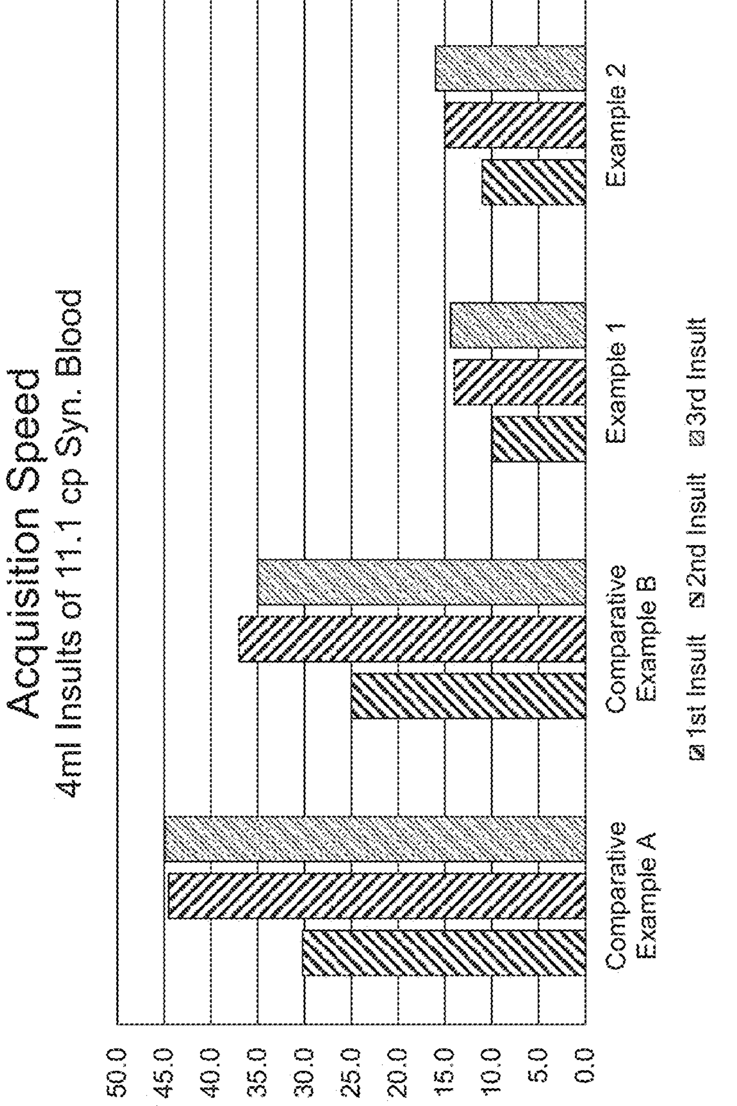
FIG. 7 is a plot of acquisition speeds of each of three insults of synthetic blood for prior art absorbent articles and absorbent articles with formed films used as fluid distribution materials according to embodiments of the invention.
Figure 8:
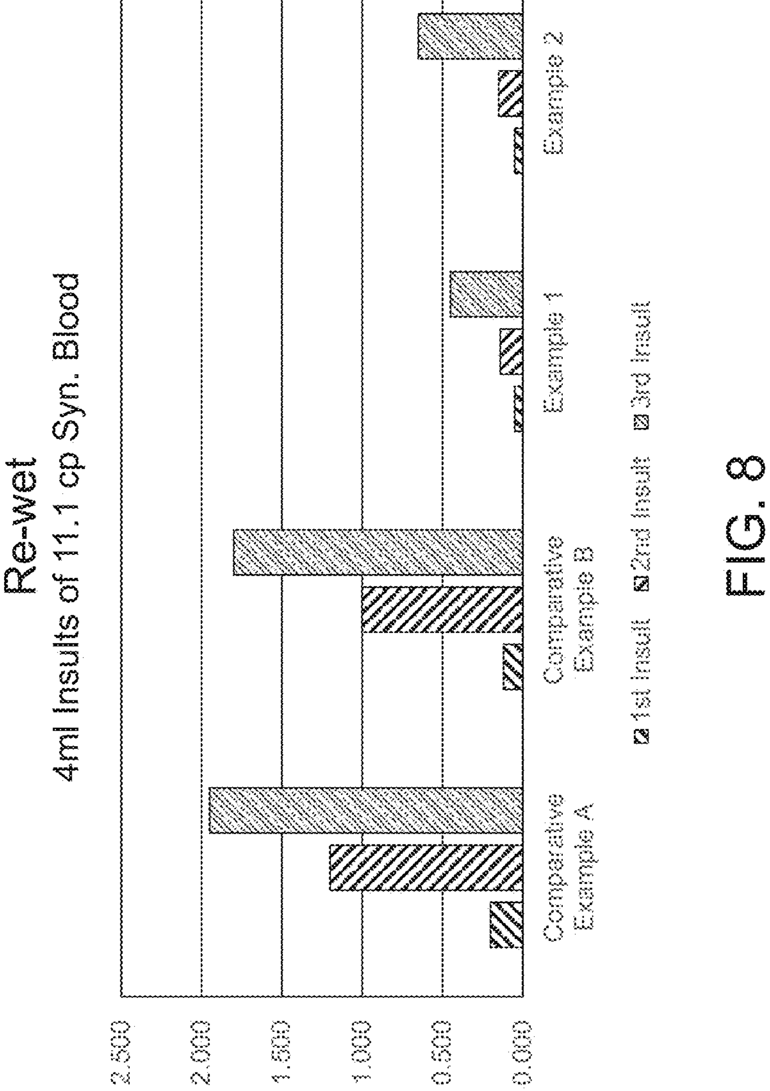
FIG. 8 is a plot of rewet values after each of three insults of synthetic blood for the prior art absorbent articles and absorbent articles with formed films used as fluid distribution materials according to embodiments of the invention.

The results of the strikethrough and rewet tests (averages of three specimens each) are illustrated in FIGS. 7 and 8. Specifically, FIG. 7 is a plot of acquisition speeds of each of the three insults of synthetic blood for the Comparative Example A, Comparative Example B, Example 1, and Example 2 pads, and FIG. 8 is a plot of rewet values after each of the three insults of synthetic blood for the same pads. Both Example 1 and Example 2 exhibited faster acquisition speeds and lower rewet values after each insult, as compared to Comparative Example A and Comparative Example B, thereby indicating improvements in removing the fluid from the topsheet and delivering the fluid to the absorbent core, as well as preventing the fluid from returning to the top of the topsheet, even while under pressure.

Returning to FIG. 4, it is noted that the thicknesses of the Example 1 and Example 2 formed films at the pressure corresponding to the insult pressure (about 0.071 psi) are significantly higher than the thickness of the Comparative STS, which provides more void volume beneath the topsheet and allows the fluid to pass through the topsheet more quickly. The thicknesses of the Example 2 formed film and the Comparative STS are about the same at the rewet pressure (about 0.6 psi), while the thickness of the Example 1 formed film is slightly higher than the thickness of the Comparative STS, yet the Example 1 and Example 2 pads exhibited much better (lower) rewet values. Not to be bound by theory, it is postulated that the reason Example 2 performed better than the Comparative STS is due to more extensive use of the absorbent core 130, or spreading, leading to additional material being bound in the absorbent core 130.

Figure 9:
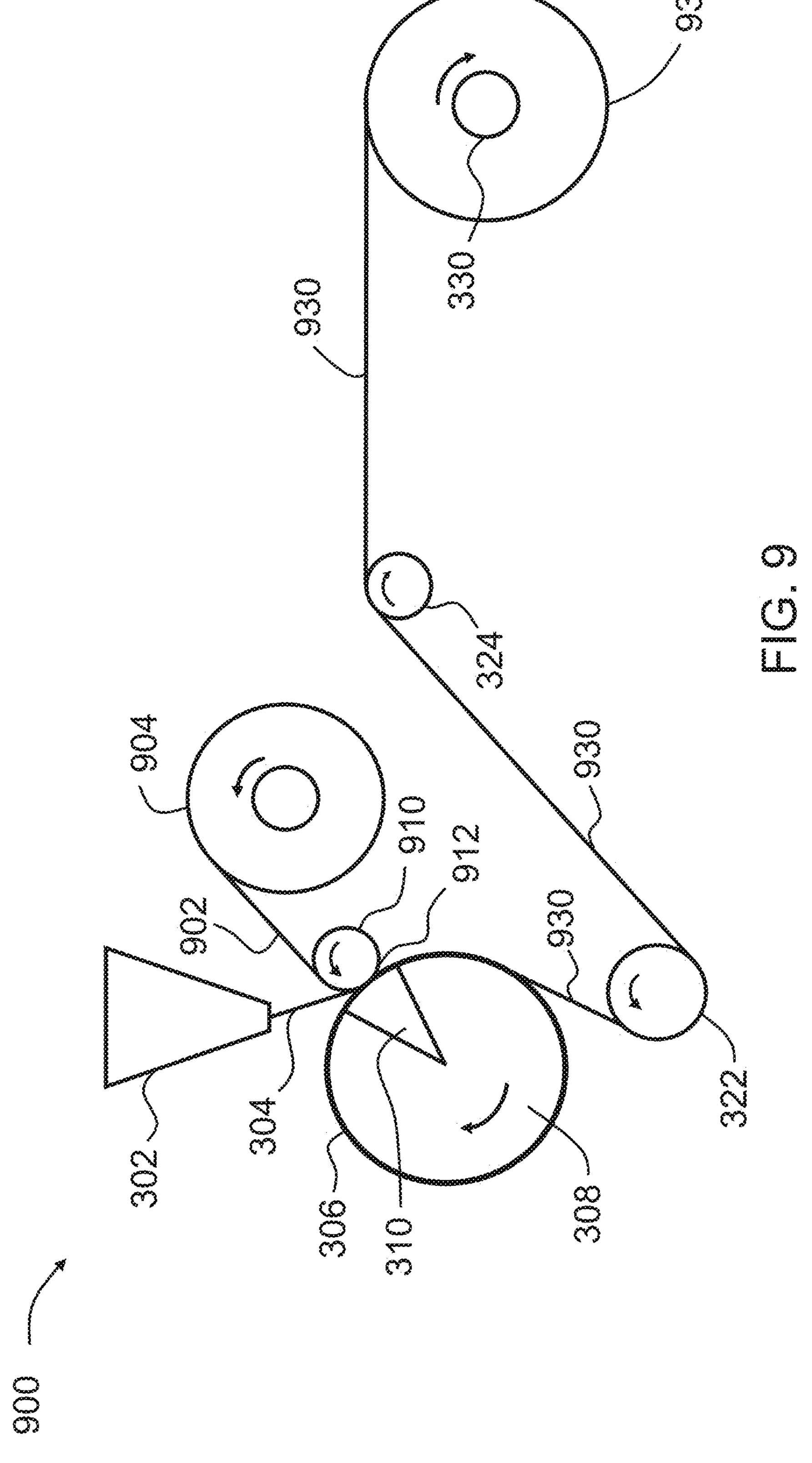
FIG. 9 is a schematic representation of an apparatus for manufacturing a laminate in accordance with embodiments of the invention.

In an embodiment, the formed film 200 may be laminated to a topsheet material so that the topsheet 110 and fluid distribution material 140 are bonded together before being assembled in the absorbent article 100, as discussed above. To this end, FIG. 9 schematically illustrates an apparatus 900 that may be used to manufacture a vacuum laminate of the topsheet 110 and the fluid distribution material 140, with the fluid distribution material being the formed film 200 described above. As illustrated, the extrusion die 302 extrudes the polymer melt curtain 304 onto the forming structure 306 as a topsheet material 902 that has been previously formed is unwound from a roll 904 using a laminating roller 910. The melt curtain 304 is still molten at an impingement point 912 between the forming structure 306 and the laminating roller 910. This allows the melt curtain 304 to bond to the topsheet material 902 while the apertures and elongated ridges are created in the melt curtain 304 to create the formed film 200 described above. The resulting topsheet/fluid distribution material laminate 930 may be wound by the winder 330 into a roll 932. The topsheet material 902 may be a formed film, a nonwoven, a film/nonwoven laminate, a film/film laminate, etc.

Figures 10A, 10B:
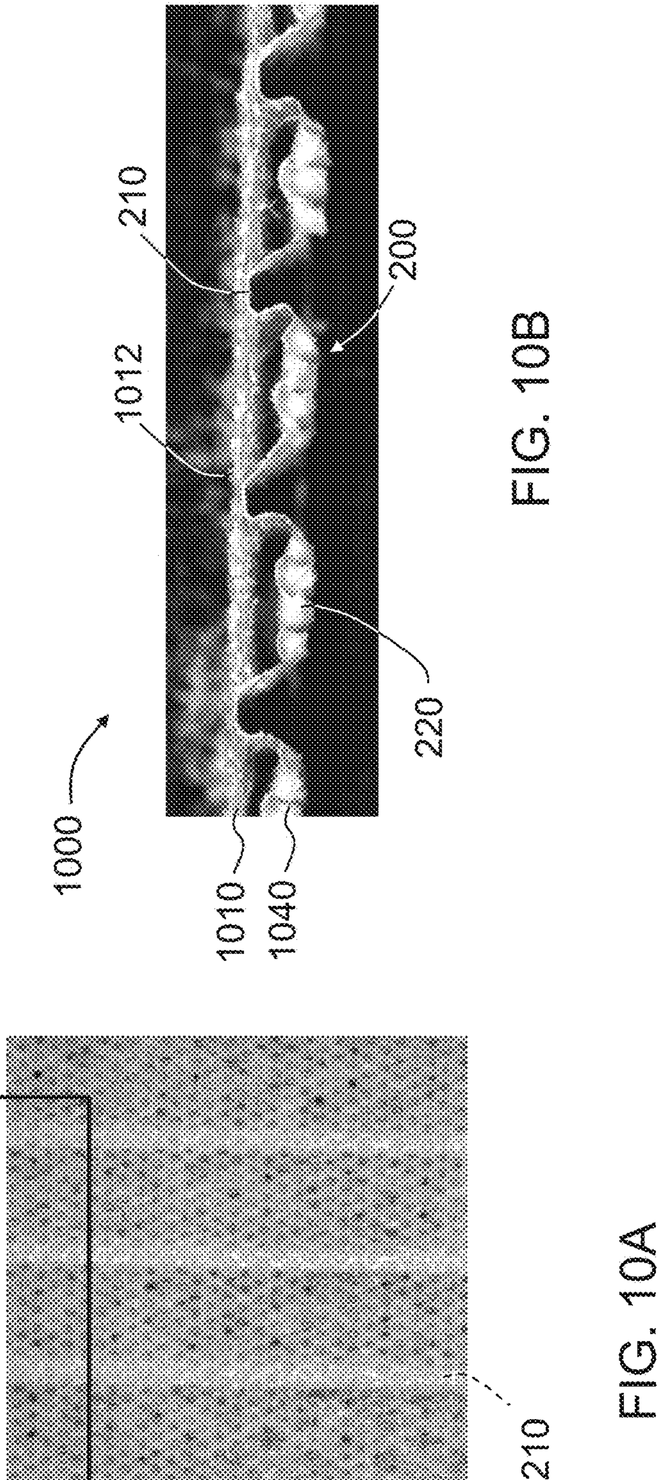
FIG. 10A is a photograph of a top view of a laminate of a topsheet/fluid acquisition layer according to an embodiment of the invention.
FIG. 10B is an enlarged photograph of a cross-section of the laminate of FIG. 10A taken along lines 10B-10B.

FIG. 10A is a photograph of a top view of a laminate 1000 of a topsheet 1010 and a fluid acquisition layer 1040 according to an embodiment of the invention, and FIG. 10B is an enlarged photograph of a cross-section of the laminate 1000 of FIG. 10A taken along lines 10B-10B. In this embodiment, the topsheet 1010 is a film/nonwoven laminate with a film layer having a plurality of apertured protuberances 1012 having a mesh count of about 60 apertured protuberances per linear inch extending away from a nonwoven layer. The fluid acquisition layer 1040 is the formed film 200 described above. Fibers of the nonwoven layer of the topsheet 1010 are embedded in the ridges 210 of the formed film 200/fluid acquisition layer 1040.

Figures 11A, 11B:
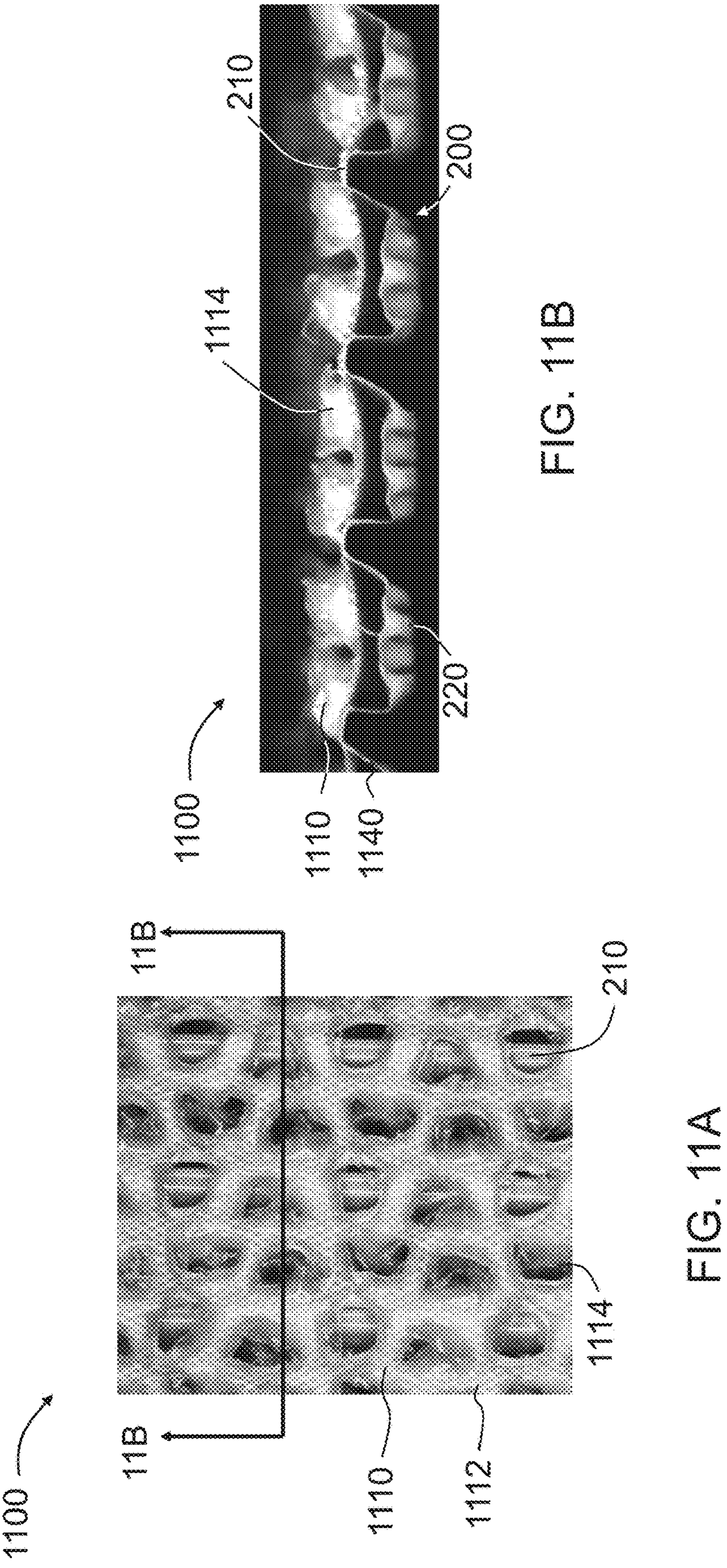
FIG. 11A is a photograph of a top view of a laminate a topsheet/fluid acquisition layer according to an embodiment of the invention.
FIG. 11B is an enlarged photograph of a cross-section of the laminate of FIG. 11A taken along lines 11B-11B.

FIG. 11A is a photograph of a top view of a laminate 1100 of a topsheet 1110 and fluid acquisition layer 1140 according to an embodiment of the invention, and FIG. 11B is an enlarged photograph of a cross-section of the laminate 1100 of FIG. 11A taken along lines 11B-11B. In this embodiment, the topsheet 1110 is a formed film having a plurality of micro protuberances 1112, which may or may not be apertured, and a plurality of macro apertured protuberances 1114. The fluid acquisition layer 1140 is the formed film 200 described above. Portions of the topsheet 1110 are bonded to the ridges 210 of the formed film 200/fluid acquisition layer 1140.

Figure 12:
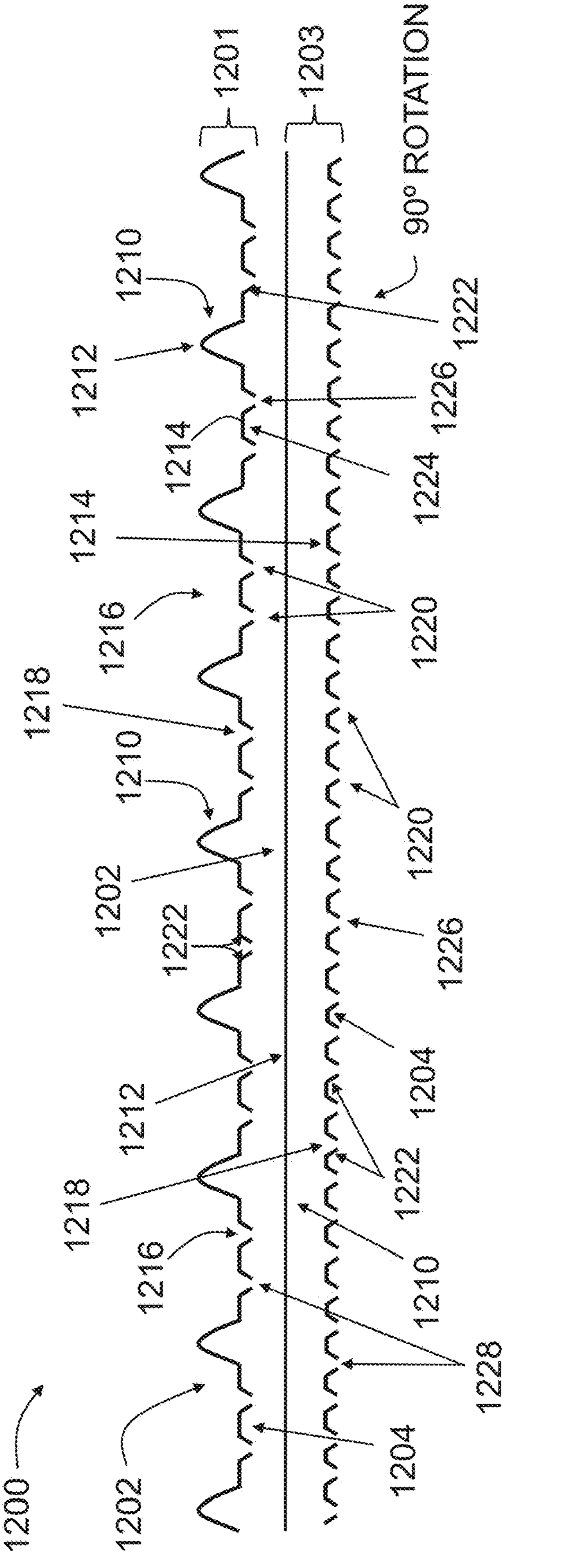
FIG. 12 is a schematic cross-sectional view of a first contemplated embodiment of a film laminate according to the present invention.

FIG. 12 is a cross-sectional, graphical representation of a first contemplated embodiment of a formed film laminate 1200 according to the present invention.

The formed film laminate 1200 is contemplated to be employed as a fluid distribution material, such as the fluid distribution material 140 in the absorbent article 100 illustrated in FIG. 1. Alternatively, it is also contemplated that the laminate 1200 may be employed as a topsheet, such as the topsheet 110 for the absorbent article 100 illustrated in FIG. 1.

It is noted that the examples of a topsheet or a fluid distribution material are merely non-limiting examples of the ways in which the formed film laminate 1200 may be employed. As such, the formed film laminate 1200 is not contemplated to be limited solely to either a topsheet or a fluid distribution material. To the contrary, the formed film laminate 1200 may be used in a wide variety of applications, as should be apparent to those skilled in the art. In particular, being a fluid distribution material, the formed film laminate 1200 may function as any layer incorporated into an absorbent article 100 where fluid permeability is required and/or desired.

It is noted, as should be apparent from the discussion herein, that the formed film laminate 1200 may be employed in articles other than an absorbent article 100 without departing from the scope of the present invention.

The formed film laminate 1200 combines a first formed film 1201 with a second formed film 1203. The first formed film 1201 is contemplated to have the same structure (or a similar structure) as the formed film 200 illustrated in FIG. 2C. Similarly, the second formed film 1203 is contemplated to have the same structure (or a similar structure) as the formed film 200 illustrated in FIG. 2C.

As shown in FIG. 12, the second formed film 1203 is not oriented in the same direction as the first formed film 1201. In this embodiment of the formed film laminate 1200, the second formed film 1203 is oriented at right angles (or 90°) with respect to the first formed film 1201.

For purposes of the present invention, it is contemplated that the first formed film 1201 and the second formed film 1203 will be rotated at an angle greater than 0° but less than or equal to 90°. The rotational offset assures that the first formed film 1201 sits atop the second formed film 1203 in a manner such that the two formed films 1201, 1203 are not in register with one another. If the first and second formed films 1201, 1203 are in register with one another, there is the possibility that the two formed films 1201, 1203 will stack directly on top of one another without any air gap therebetween. Still further, to assure a suitable rotational offset between the first formed film 1201 and the second formed film 1203, it is contemplated that the rotational offset will be greater than or equal to 5° and less than or equal to 90°.

In an alternative construction, the second formed film 1203 may have a 0° rotation but be offset laterally from the first formed film 1201.

The first formed film 1201 and the second formed film 1203 may be bonded to one another by any means known to those skilled in the art. The bonds may be formed, for example, via adhesive bonding, thermal bonding, thermal point bonding, sonic bonding and the like. Still further, it is contemplated that the first formed film 1201 and the second formed film 1203 may be connected to one another at the edges.

As illustrated in FIG. 12, the first formed film 1201 includes a first side 1202 (or first surface 1202) and a second side 1204 (or second surface 1204). Similarly, the second formed film 1203 includes a first side 1202 and a second side 1204.

Since the first formed film 1201 and the second formed film 1203 are contemplated to share the same (or a similar construction), the first and second formed films 1201, 1203 incorporate protrusions in the form of elongated ridges 1210 that extend along a direction D1, consistent with FIG. 2A. The elongated ridges 1210 have peaks 1212 that are vertically spaced apart from first land areas 1214 by the distance h1 as discussed in connection with FIG. 2D. The first sides 1202 of the first and second formed films 1201, 1203 also include a plurality of valleys 1216 that are defined by adjacent elongated ridges 1210 and the first land areas 1214. The valleys 1216 alternate with the elongated ridges 1210 in the second direction D2, orthogonal to the first direction D1, as discussed hereinabove. The first sides 1202 of the first and second formed films 1201, 2013 also include primary apertures 1218 that are consistent with the primary apertures 218 described in connection with the formed film 200.

The second sides 1204 of the first and second formed films 1201, 1203 of the formed film laminate 1200 include a plurality of apertured protuberances 1220. Each apertured protuberance 1220 is defined by continuous sidewalls 1222 that extend away from the second land areas 1224 to distal ends 1226. The distal ends 1226 include secondary apertures 1228 that are substantially aligned with the primary apertures 1218. The distal ends 1226 are spaced apart from the second land areas 1224 by the distance h2.

As before, the first formed film 1201 and the second formed film 1203 individually have a thickness ET that is the sum of the nominal thickness t of the film between the first and second land areas 1214, 1224, the height h1 of the elongated ridges 1210, and the height h2 of the apertured protuberances 1220.

In the illustrated embodiment, the apertured protuberances 1220 are arranged in a pattern having about 5 to about 45 protuberances per linear inch or "mesh," i.e., about 5 mesh to about 45 mesh in at least one direction. As before, the pattern may be a hexagonal pattern, a square pattern, a staggered pattern, or any other type of pattern or design.

In addition, it is noted that the apertured protuberances 1220, including the primary apertures 1218 and the secondary apertures 1228 are illustrated as being circular. It is noted that a circular construction is merely exemplary of the shape of the apertures 1218, 1228. The apertures may be triangular, square, rectangular, elliptical, and/or amorphously shaped, for example, without departing from the scope of the present invention.

The polymer(s) of the first and second formed films 1201, 1203 are contemplated to be the same as other embodiments, including the formed film 200, described herein. As discussed in connection with the formed film 200, the formed films 1201, 1203 are contemplated to have a basis weight of between about 14 gsm to about 45 gsm. Alternatively, the first and second formed films 1201, 1203 may have a basis weight of between about 20 and about 35 gsm.

As illustrated in FIG. 12, the first sides 1202 of the first formed film 1201 and the second formed film 1203 are oriented so that the first sides 1202 are both oriented away from the garment facing side of the laminate 1200. In other words, in the illustrated embodiment, the first sides 1202 are contemplated to face away from a garment worn by a user. Conversely, the second sides 1204 are contemplated to be garment facing.

It is noted that the disposition of the first formed film 1201 with respect to the second film 1203 is merely one contemplated arrangement for the formed film laminate 1200 according to the present invention. It is also contemplated that the second formed film 1203 may be turned upside down with respect to the orientation illustrated in FIG. 12. If so, the second side 1204 of the second formed film 1203 is contemplated to face the second side 1204 of the first formed film 1201. As should be apparent, in this contemplated embodiment, the apertured protuberances 1220 of the first and second formed films 1201, 1203 will be disposed in a facing orientation such that they are disposed adjacent to one another.

Figure 13:
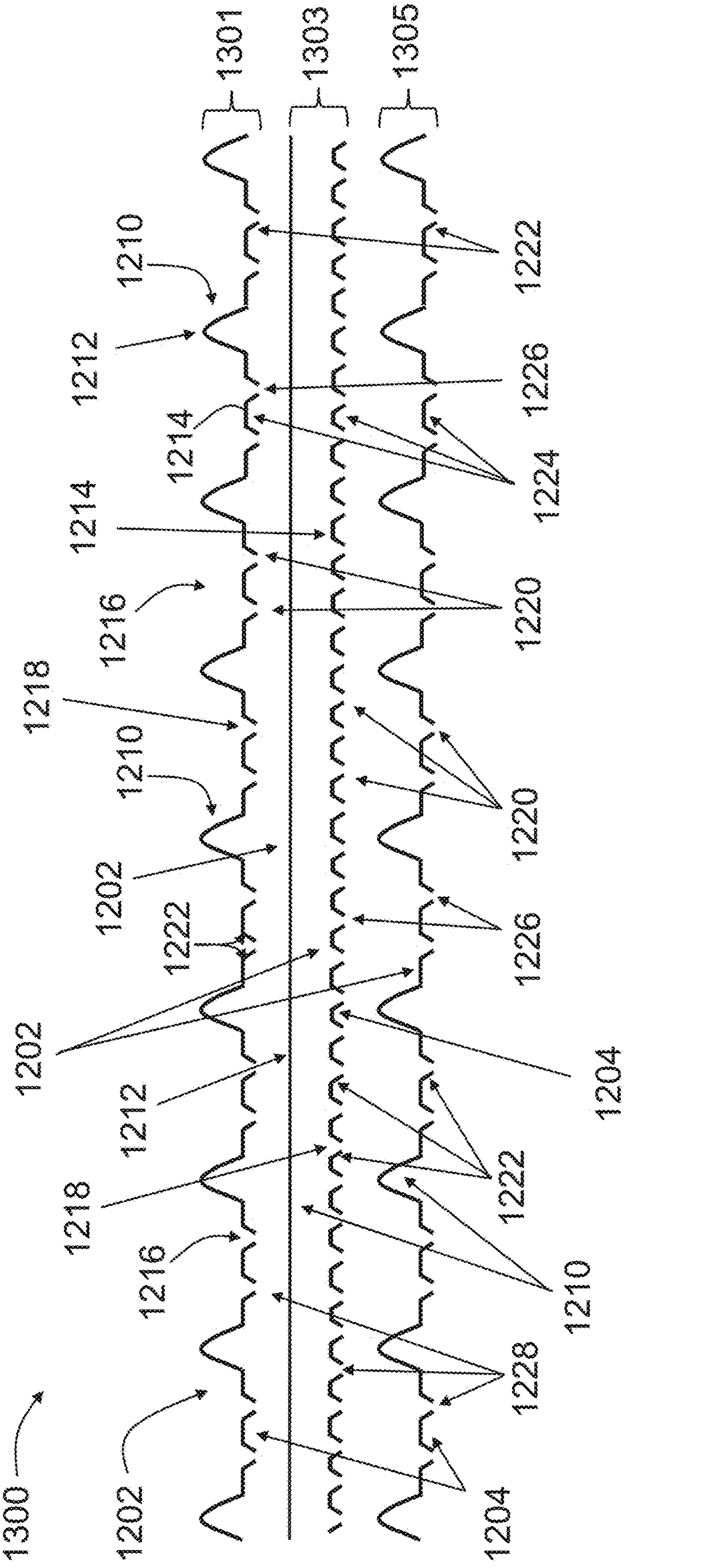
FIG. 13 is a schematic cross-sectional view of a second contemplated embodiment of a film laminate according to the present invention.

FIG. 13 is a cross-sectional, graphical representation of a second contemplated embodiment of a formed film laminate 1300 according to the present invention.

The formed film laminate 1300 is contemplated to combine a first formed film 1301, a second formed film 1303, and a third formed film 1305.

The first formed film 1301 and the second formed film 1303 are contemplated to have the same construction and orientation of the first formed film 1201 and the second formed film 1203 illustrated in FIG. 12. The third formed film 1305 is contemplated to have the same construction and orientation as the first formed film 1201 illustrated in FIG. 12. As such, a detailed discussion of the constructions of the first, second, and third formed films 1301, 1303, 1305 is not provided here. Instead, reference is made to the discussion of the first and second formed films 1201, 1203 provided in connection with the formed film laminate 1200 provided in connection with FIG. 12.

As illustrated in FIG. 13, the first formed film 1301 and the third formed film 1305 are oriented in the same directions. As in the prior example, the second formed film 1303 is oriented 90° with respect to the first formed film 1301 and the third formed film 1305.

As also illustrated, all of the first sides 1202 of the first, second, and third formed films 1301, 1303, and 1305 are body facing. As such, all of the second sides 1204 of the first, second, and third formed films 1301, 1303, and 1305 are garment facing.

As discussed in connection with the formed film laminate 1200, the present invention also contemplates that one or more of the first, second, and third formed films 1301, 1303, and 1305 will be flipped over so that the first side 1202 is upside down by comparison with the orientations illustrated in FIG. 13. In other words, the arrangement of the first, second, and third formed films 1301, 1303, and 1305 as shown in FIG. 13 is merely exemplary of the present invention. The construction of the formed film laminate 1300 is, therefore, a non-limiting example.

Still further, while the first, second, and third formed films 1301, 1303, 1305 are show as being rotated 90° with respect to one another, this rotational orientation is not required to practice the present invention. In one contemplated variation, for example, the second formed film 1303 is rotated 45° with respect to the first formed film 1301 and the third formed film 1305 is rotated 15° with respect to the second formed film 1303. As before, it is contemplated that the adjacent ones of the formed films 1301, 1303, 1305 will be rotated to an amount greater than 0° but less than 90°. Also as discussed in connection with the formed film laminate 1200, adjacent ones of the formed films 1301, 1303, 1305 are contemplated to be rotated to an amount greater than or equal to 5° and less than or equal to 90°.

The formed film laminate 1300 is contemplated to be used in the same way as the laminate 1200. For example, the laminate 1300 is contemplated to be employed as a fluid distribution material 140 or as a topsheet 110. As with the formed film laminate 1200, these uses are merely provided as non-limiting examples of the ways in which the formed film laminate 1300 may be utilized. Like the formed film laminate 1200, the formed laminate 1300 is contemplated to be used in any of a wide variety of applications, as should be apparent to those skilled in the art.

In connection with the discussion of the formed film laminates 1200, 1300, the first, second, and third formed films 1201, 1301, 1203, 1303, and 1305 are arranged so that the second formed films 1203, 1303 are rotated by 90° with respect to the remaining formed films 1201, 1301, 1305. This arrangement is merely exemplary of one arrangement contemplated for the present invention, as noted above.

It is contemplated that the first, second, and third formed films 1201, 1301, 1203, 1303, and 1305 may be rotated or any angular orientation between 0° and 90° without departing from the scope of the present invention. For example, in one contemplated embodiment, the second formed film 1203, 1303 may be rotated 45° with respect to the first formed film 1201, 1301. In a contemplated embodiment for the formed film laminate 1300, the second formed film 1303 is rotated 45° with respect to the first formed film 1301 and the third formed film 1305 is rotated 45° with respect to the second formed film 1303. Therefore, in this contemplated embodiment, the third formed film 1305 is rotated 90° with respect to the first formed film 1301.

FIGS. 14, 15, 17, 18, and 19 illustrate further examples of formed films that are contemplated to be employed alone or as a part of a formed film laminate.

Figure 14:
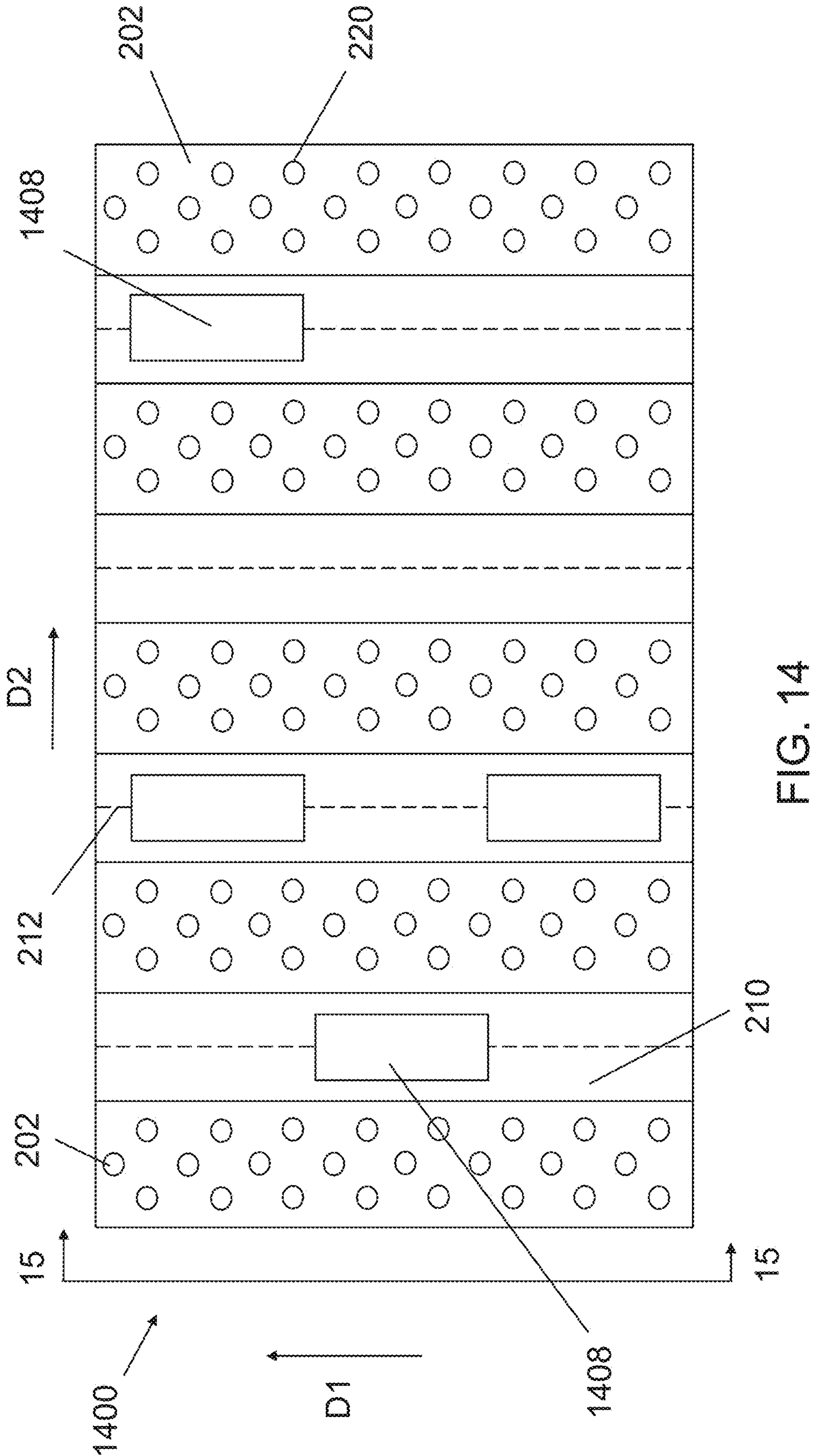
FIG. 14 is a graphical top view of a third embodiment of a formed film according to the present invention.

FIG. 14 illustrates a further embodiment of a formed film 1400 according to the present invention.

The formed film 1400 is contemplated to be nearly the same construction as the formed film 200. However, in this embodiment, the elongated ridges 210 are provides with depressed regions 1408. The depressed regions 1408 are regions where the elongated ridges 210 have a height less than the height h1.

Figure 15:
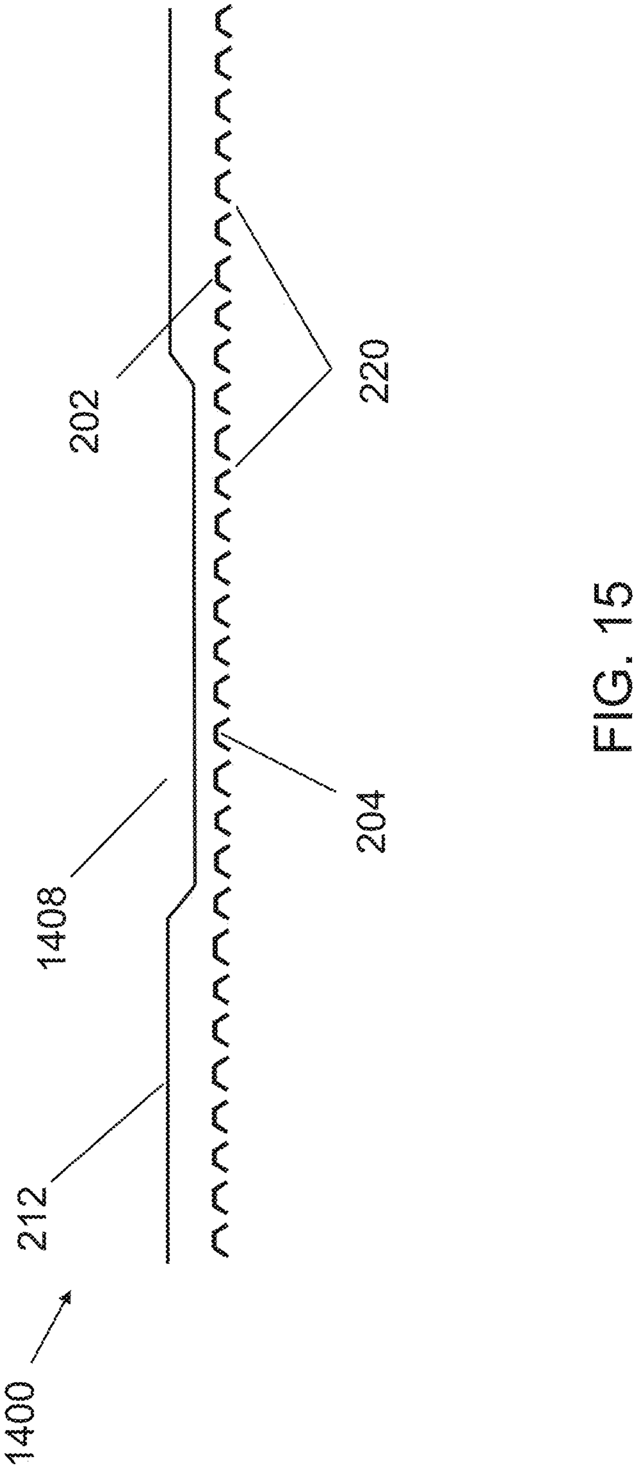
FIG. 15 is a graphical side view of the formed film illustrated in FIG. 14.

FIG. 15 is a side view of the formed film 1400 illustrated in FIG. 14. The side view is shown as the formed film 1400 would appear if viewed edge-on from the line designated 15-15 in FIG. 14. The configuration of one of the depressed regions 1408 is more easily identified in this view.

It is noted that the depressed region 1408 is illustrated as being of a particular height. However, this is intended to be a non-limiting example of the depth of the depressed region 1408. The depressed region 1408 may have any depth between 0-h1.

Also as illustrated in FIG. 14, the depressed regions 1408 may be positioned at any of a number of locations within the elongated ridges 210 of the formed film 1400. The depressed regions 1408 may be located at regular intervals along the elongated ridges 210. Alternatively, the depressed regions 1408 may be located in an irregular pattern in one or more of the elongated ridges 210.

Figure 16:
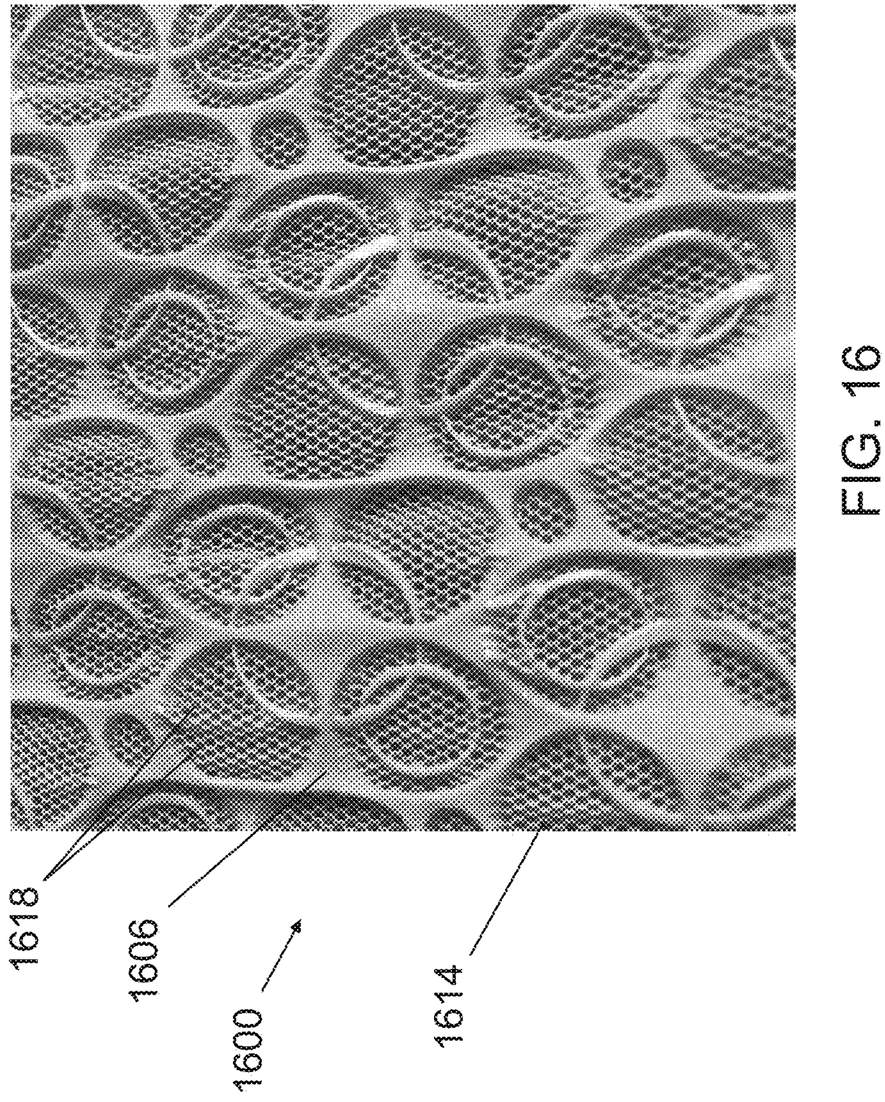
FIG. 16 is a photograph of a formed film including a plurality of pockets.
Figure 17:
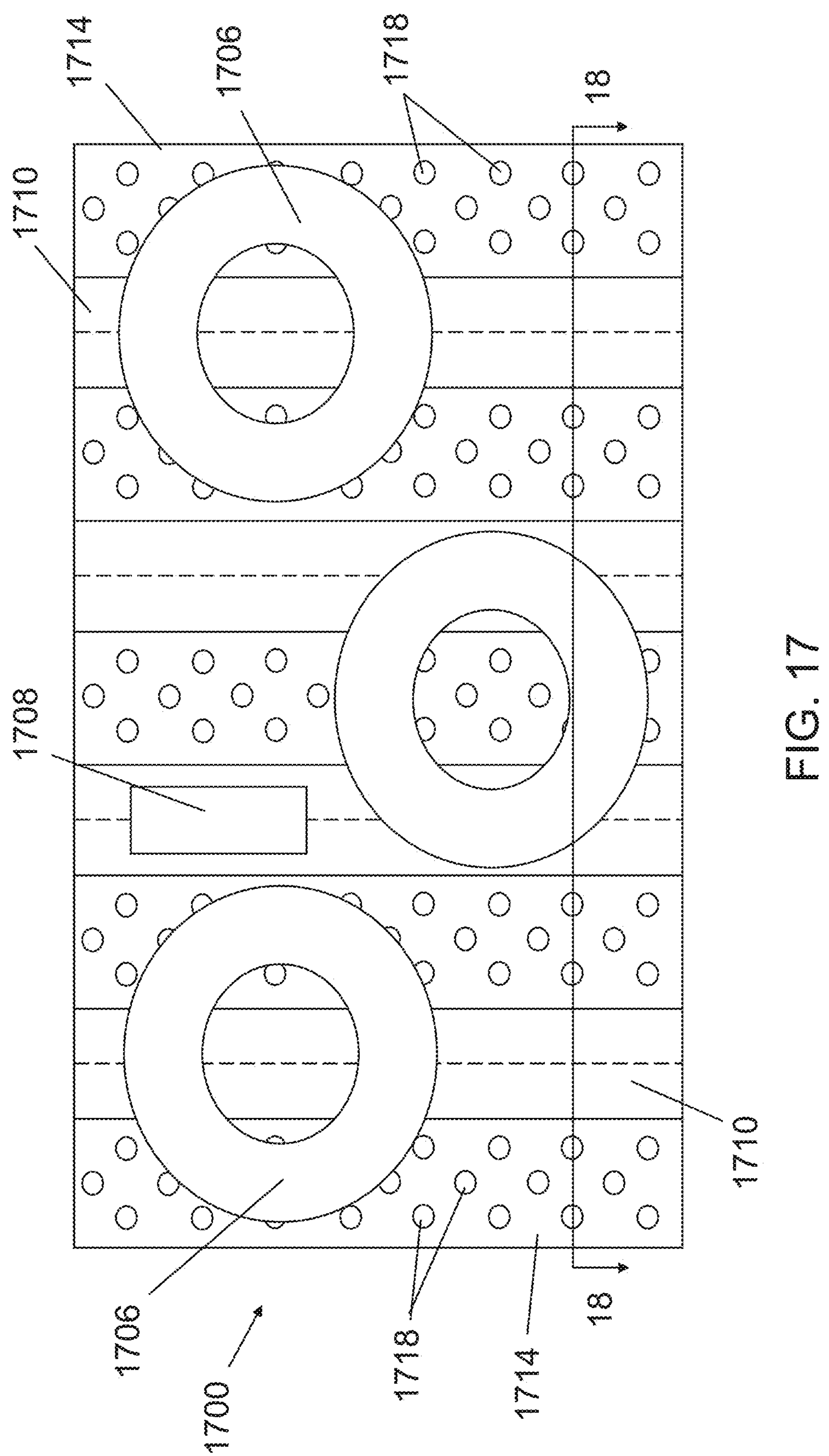
FIG. 17 is a graphical top view of a third contemplated embodiment of a formed film according to the present invention.
Figure 18:
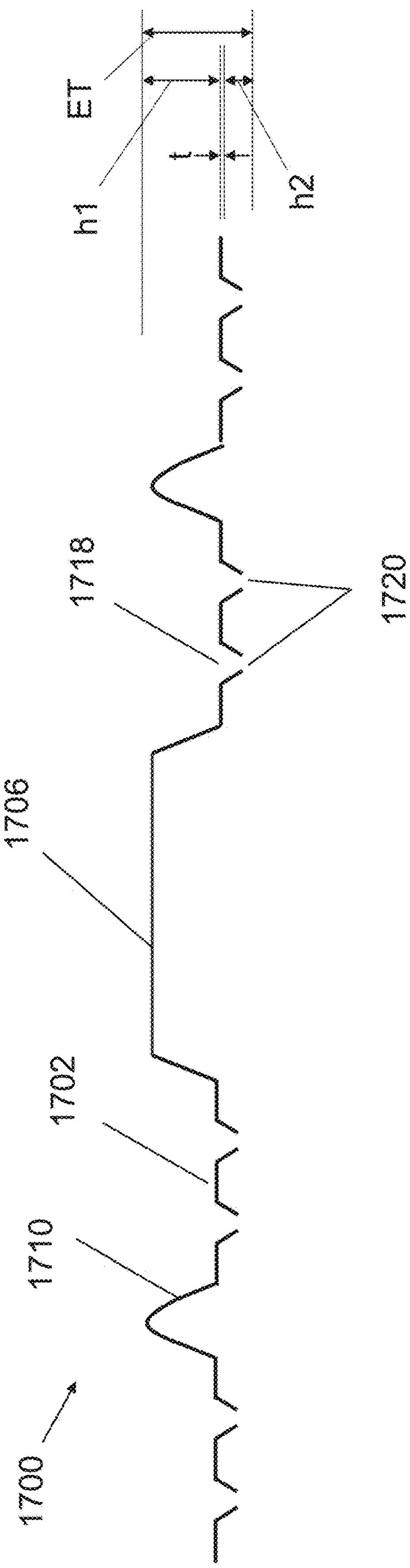
FIG. 18 is a cross-sectional side view of the formed film illustrated in FIG. 17.
Figure 19:
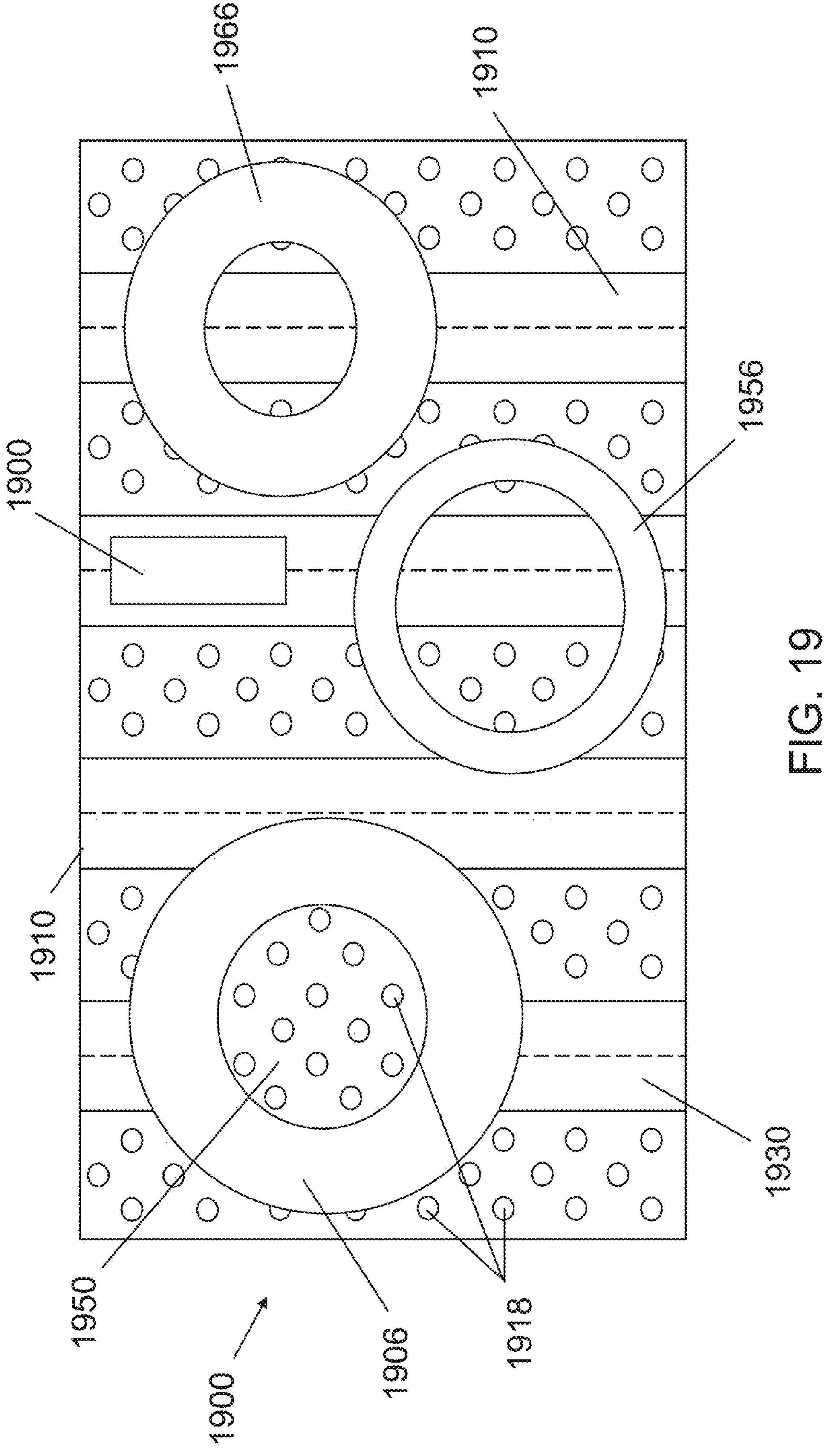
FIG. 19 is a graphical top view of a fourth contemplated embodiment of a formed film according to the present invention.

FIG. 16 is a photograph of an example of an apertured, formed film 1600 that provides a framework for the discussion of FIGS. 17-19.

As shown in FIG. 16, the formed film 16 includes first land areas 1614 and pocket regions 1606. The first land areas 1614 include primary apertures 1618 like the primary apertures 218 discussed in connection with the formed film 200. The pocket regions 1606 are unapertured. The pocket regions 1606 have a height that is above the first land areas 1614 that include the primary apertures 1618.

The formed film 1600 does not include elongated ridges. As a result, it is noted that the formed film 1600 has a tendency to wrinkle, as depicted in FIG. 16. To avoid wrinkling, the elongated ridges are preferred to be added, as discussed herein.

FIG. 17 is a graphical, top view of a formed film 1700 according to another embodiment of the present invention.

In this embodiment, the formed film 1700 includes elongated ridges 1710 that are similar to the elongated ridges 210 discussed in connection with the formed film 200. The first land areas 1714 include primary apertures 1718.

The formed film 1700 also includes pocket regions 1706. In this embodiment, the pocket regions 1706 are illustrated as donut shaped regions in the formed film. The pocket regions 1706 are not apertured. FIG. 17 also illustrates one depressed region 1708, which is understood to be consistent with the depressed regions 1408 discussed in connection with FIGS. 14 and 15.

FIG. 18 is a cross-sectional side view of the formed film illustrated in FIG. 17. The profile of the pocket region 1706 is highlighted. In addition, the shapes of the apertured protuberances 1720 also are illustrated.

FIG. 19 is a graphical, top view of another embodiment of a formed film 1900 according to the present invention.

This embodiment incorporates continuous elongated ridges 1910 and one discontinuous elongated ridge 1930. The discontinuous elongated ridge 1930 does not extend along the entire length (or width) of the formed film 1900. The continuous elongated ridges 1910 extend along an entire length (or width) of the formed film 1900. As shown here, the formed film 1900 includes an intermediate land area 1950 with primary apertures 1918 at the center of one of the pocket regions 1906, 1956, 1966 incorporated into the formed film 1900. The formed film 1900 also includes one depressed region 1908, which is understood to be consistent with the depressed regions 1408 discussed in connection with FIGS. 14 and 15.

In this embodiment of the formed film 1900, the pocket regions 1906, 1956, 1966 are not the same size. It is noted that, while shown as being donut shaped, the pocket regions 1906, 1956, 1966 may have any shape and/or configuration without departing from the scope of the present invention.

As discussed in connection with FIGS. 12 and 13, the present invention is contemplated to encompass a formed film laminate 1200, 1300 that combined two or more formed films 1201, 1203, 1301, 1303, 1305, 1400, 1700, 1900 as discussed herein.

In addition, one or more of the formed films 1201, 1203, 1301, 1303, 1305, 1400, 1700, 1900 may be combined with a nonwoven. In other words, one or more of the formed films 1201, 1203, 1301, 1303, 1305, 1400, 1700, 1900 also may be combined with a nonwoven material/layer. The nonwoven material/layer is contemplated to be connected to the formed films 1201, 1203, 1301, 1303, 1305, 1400, 1700, 1900 via adhesive bonding, thermal bonding, thermal point bonding, sonic bonding and the like.

Individually, the formed films 1201, 1203, 1301, 1303, 1305, 1400, 1700, 1900 are contemplated to behave in the manner discussed in connection with, for example, the formed film 200. As such, the formed films 1201, 1203, 1301, 1303, 1305, 1400, 1700, 1900 may be employed in the same manner as discussed in connection with the formed film 200.

Still further, it is noted that, when two or more of the formed films 200, 1201, 1203, 1301, 1303, 1305, 1400, 1700, 1900 are combined into a formed film laminate, such as the formed film laminates 1200, 1300, the formed film laminates 1200, 1300 not only provide excellent fluid distribution and dryness properties, the formed film laminates also provide a high loft that exhibits excellent compressibility properties.

Concerning the loft of the formed film laminates 1200, 1300, it is contemplated that the formed film laminates 1200, 1300 will present a loft between about 1.5 mm-5.0 mm. Other end points for the loft of the formed film laminate 1200, 1300 include, but are not limited to 1.5 mm, 1.75 mm, 2.0 mm, 2.25 mm, 2.5 mm, 2.75 mm, 3.0 mm, 3.25 mm, 3.5 mm, 3.75 mm, 4.0 mm, 4.25 mm, 4.5 mm, 4.75 mm, and 5.0 mm. As such, one contemplated range for the loft of the formed film laminate 1200, 1300 includes a range of 1.5-3.5 mm. It is contemplated that one suitable range for the formed film laminate is 2.0 mm-3.0 mm.

As noted hereinabove, loft is a desirable property for a topsheet 110 and/or a fluid distribution material 140, because a higher loft results in a material that is softer to the touch. As also noted hereinabove, the prior art has struggled with the development of a high loft material for an absorbent article 100, because higher lofts typically are also associated with poorer fluid distribution.

The formed films 200, 1201, 1203, 1301, 1303, 1305, 1400, 1700, 1900 of the present invention exhibit excellent fluid distribution properties. These properties are retained even when the formed films 200, 1201, 1203, 1301, 1303, 1305, 1400, 1700, 1900 are combined together to create a formed film laminate 1200, 1300. As such, the formed film laminates 1200, 1300 of the present invention provide not only a high loft, but also provide excellent fluid distribution properties.

For the present invention, it is noted that the term "high loft" is intended to encompass any material with a thickness of 1.0 mm or more.

The formed film laminates 1200, 1300 of the present invention also exhibit excellent compression and recovery properties.

"Compression" refers to the property of a material when that material is subjected to a compressive force. Specifically, when a material is subjected to a compressive force, the material typically will collapse under the compressive force. The higher the compressibility of the material, the less desirable the material is for a topsheet 110 or a fluid distribution material 140.

One reason that a highly (or easily) compressible material is less desirable is that the material, when highly compressed, loses a "soft" tactile feeling. This is considered to be undesirable for absorbent articles 100. When a person wearing an absorbent article 100 sits down, if the material compresses too much, the absorbent article 100 will become less comfortable.

"Recovery" refers to the property of a material to recover its loft after having been compressed. As should be apparent, it is desirable for a material to have as high a recovery as possible so that the material retains a suitable compressibility and, therefore, retains a soft feeling during the time that the absorbent article 100 is worn by a user.

Figure 20:
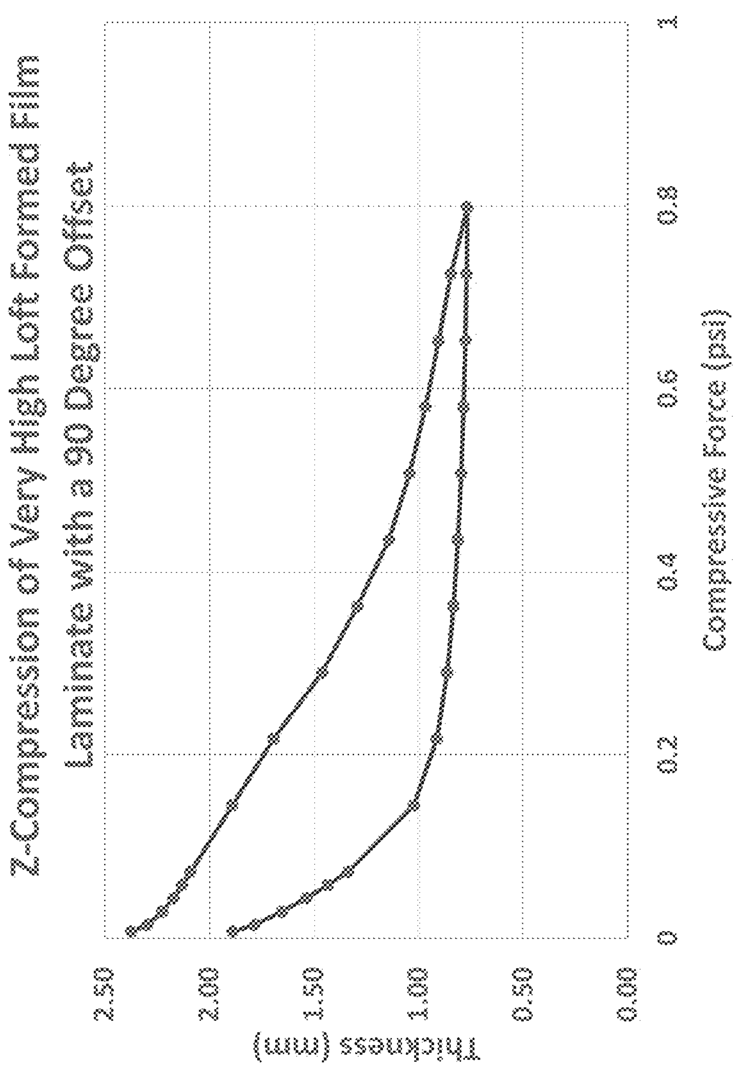
FIG. 20 is a graph that plots a compression/recovery curve for the formed film laminate illustrated in FIG. 12.
Figure 21:
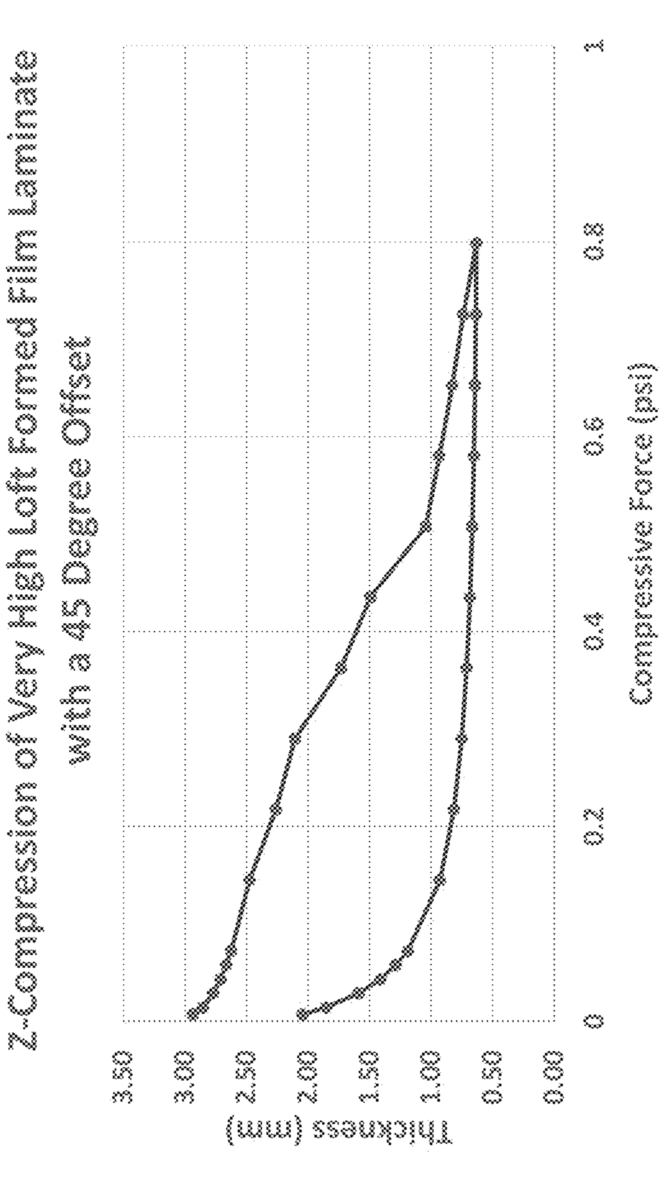
FIG. 21 is a graph that plots a compression/recovery curve for another formed film laminate according to the present invention.

FIGS. 20 and 21 are graphs that plot the thickness (mm) of a formed film laminate in accordance with the present invention against the compressive force applied to the formed film laminate.

With respect to both plots. It is noted that the top (or superior) curve plots the thickness of the formed film laminate against the compressive force during the time when the formed film laminate is compressed for the first time. The bottom (or inferior) curve plots the thickness of the formed film laminate during recovery, thereby reporting the recovery forces applied as the compressive force was reduced from a maximum value. As indicated, the thickness of the formed film laminate is measured in mm. The compressive force and the recovery forces are measured in pounds per square inch (or psi).

To measure the thickness values, a compression testing apparatus made by Thwing-Albert Instrument Company (with a business address at 14 West Collings Ave., West Berlin, New Jersey 08091, USA) was employed. In particular, the Vantage NX compression testing unit was used. The Vantage NX compression testing unit had Instrument Model No. 1900-2008.

FIG. 20 illustrates the compression and recovery data for the formed film laminate 1200. As discussed above, the formed film laminate 1200 includes a second formed film 1203 with a 90° offset.

In FIG. 20, the formed film laminate 1200 displays an excellent compressibility and an excellent recovery, which supports the suitability of the formed film laminate 1200 for use as a topsheet 110, a fluid distribution material 140, or other material incorporated into an absorbent article 100. The data underlying the graph provided in FIG. 20 is provided below in Table 1.

TABLE 1

Very High Loft Formed Fim Laminate With a 90 Degree Offset (No Adhesive)

| Compression Data | | Recover Data | |
|---|---|---|---|
| Compressive Force psi | Thickness mm | Recovery Force psi | Thickness mm |
| 0.0073 | 2.371 | 0.7980 | 0.767 |
| 0.0145 | 2.294 | 0.7250 | 0.770 |
| 0.0290 | 2.223 | 0.6525 | 0.777 |
| 0.0435 | 2.172 | 0.5800 | 0.785 |
| 0.0580 | 2.128 | 0.5075 | 0.796 |
| 0.0725 | 2.088 | 0.4350 | 0.812 |
| 0.1450 | 1.889 | 0.3625 | 0.833 |
| 0.2175 | 1.693 | 0.2900 | 0.863 |
| 0.2900 | 1.461 | 0.2175 | 0.912 |
| 0.3625 | 1.292 | 0.1450 | 1.023 |
| 0.4350 | 1.142 | 0.0725 | 1.337 |
| 0.5075 | 1.043 | 0.0580 | 1.432 |
| 0.5800 | 0.967 | 0.0435 | 1.537 |
| 0.6525 | 0.904 | 0.0290 | 1.653 |
| 0.7250 | 0.845 | 0.0145 | 1.783 |
| 0.7980 | 0.767 | 0.0073 | 1.888 |

For the plot illustrated in FIG. 20, the first formed film 1201 was overlayed over the second formed film 1203. No adhesive was used to connect the first formed film 1201 to the second formed film 1203.

As noted above, the formed film laminate may be configured with two formed films, one of which is rotated 45° with respect to the other. The compression and recovery for this construction is illustrated in FIG. 21.

FIG. 21 illustrates the compression and recovery data for the formed film laminate with a 45° offset.

In FIG. 21, the formed film laminate also displays an excellent compressibility and an excellent recovery, which supports the suitability of the formed film laminate for use as a topsheet 110, a fluid distribution material 140, or other material incorporated into an absorbent article 100. The data underlying the graph provided in FIG. 21 is provided below in Table 2.

TABLE 2

Very High Loft Formed Fim Laminate With a 45 Degree Offset (No Adhesive)

| Compression Data | | Recover Data | |
|---|---|---|---|
| Compressive Force psi | Thickness mm | Recovery Force psi | Thickness mm |
| 0.0073 | 2.934 | 0.7980 | 0.634 |
| 0.0145 | 2.853 | 0.7250 | 0.637 |
| 0.0290 | 2.770 | 0.6525 | 0.644 |
| 0.0435 | 2.711 | 0.5800 | 0.654 |
| 0.0580 | 2.665 | 0.5075 | 0.667 |
| 0.0725 | 2.624 | 0.4350 | 0.685 |
| 0.1450 | 2.473 | 0.3625 | 0.712 |
| 0.2175 | 2.261 | 0.2900 | 0.752 |
| 0.2900 | 2.105 | 0.2175 | 0.816 |
| 0.3625 | 1.732 | 0.1450 | 0.928 |
| 0.4350 | 1.493 | 0.0725 | 1.190 |
| 0.5075 | 1.044 | 0.0580 | 1.286 |
| 0.5800 | 0.934 | 0.0435 | 1.411 |
| 0.6525 | 0.829 | 0.0290 | 1.588 |
| 0.7250 | 0.739 | 0.0145 | 1.853 |
| 0.7980 | 0.634 | 0.0073 | 2.045 |

For the plot illustrated in FIG. 21, the first formed film was overlayed over the second formed film. No adhesive was used to connect the first formed film to the second formed film.

As should be apparent from the foregoing, the present invention encompasses, inter alia, two formed films that are rotationally offset with respect to one another. This combination of features contributes to the creation of a high loft material having excellent dryness and compressibility features.

The embodiments described herein represent a number of possible implementations and examples and are not intended to necessarily limit the present disclosure to any specific embodiments. Instead, various modifications can be made to these embodiments, and different combinations of various embodiments described herein may be used as part of the invention, even if not expressly described, as would be understood by one of ordinary skill in the art. Any such modifications are intended to be included within the spirit and scope of the present disclosure and protected by the following claims.

What is claimed is:

1. A formed film laminate, comprising:

a first formed film comprising a first side comprising a plurality of first protrusions in the form of first elongated ridges having first peaks extending from a first land area of the first side and oriented in a first direction, a plurality of first valleys defined by adjacent first protrusions and the first land area and oriented in the first direction, and a plurality of first primary apertures located at bottoms of the first valleys; and a second side opposite the first side, the second side comprising a plurality of first apertured protuberances, each of the first apertured protuberances comprising a first continuous sidewall extending from a second land area of the second side to a first distal end comprising a first secondary aperture, wherein each first secondary aperture is substantially aligned with a first primary aperture, wherein the first formed film has a thickness greater than about 0.9 mm under a pressure of 0.071 psi, and a thickness greater than about 0.3 mm under a pressure of 0.6 psi, wherein the plurality of first protrusions excludes the plurality of first primary apertures and the plurality of first apertured protuberances, wherein the plurality of first protrusions are narrower than the plurality of first valleys, and wherein the first peaks are spaced from the first land area by a first distance that is uniform from a first end to a second end in the first direction; and a second formed film comprising a third side comprising a plurality of second protrusions in the form of second elongated ridges having second peaks extending from a third land area of the third side and oriented in the first direction, a plurality of second valleys defined by adjacent second protrusions and the third land area and oriented in the first direction, and a plurality of second primary apertures located at bottoms of the second valleys; and a fourth side opposite the third side, the fourth side comprising a plurality of second apertured protuberances, each of the second apertured protuberances comprising a second continuous sidewall extending from a fourth land area of the fourth side to a second distal end comprising a second secondary aperture, wherein each second secondary aperture is substantially aligned with a second primary aperture, wherein the second formed film has a thickness greater than about 0.9 mm under a pressure of 0.071 psi, and a thickness greater than about 0.3 mm under a pressure of 0.6 psi, wherein the plurality of second protrusions excludes the plurality of second primary apertures and the plurality of second apertured protuberances, wherein the plurality of second protrusions are narrower than the plurality of second valleys, and wherein the second peaks are spaced from the third land area by a third distance that is uniform from a third end to a fourth end in the first direction;

wherein the first formed film and the second formed film are rotationally offset by an angle greater than 0° and less than or equal to 90°.

2. The formed film laminate according to claim 1, wherein the first formed film has a basis weight between about 14 gsm and about 45 gsm.

3. The formed film laminate according to claim 1, wherein the second formed film has a basis weight between about 14 gsm and about 45 gsm.

4. The formed film laminate according to claim 1, wherein the plurality of first and second apertured protuberances are arranged in a pattern having about 5 to about 45 apertured protuberances per linear inch in the first direction.

5. The formed film laminate according to claim 1, wherein the first and second plurality of apertured protuberances are spaced from the second land area and the fourth land area, respectively, by a second distance.

6. The formed film laminate according to claim 5, wherein the first distance is greater than the second distance.

7. The formed film laminate according to claim 1, wherein the first and second primary apertures comprise more than one first and second primary aperture between adjacent peaks in a second direction orthogonal to the first direction.

8. The formed film laminate according to claim 1, further comprising:

at least one recessed region in at least one of the first and second elongated ridges.

9. The formed film according to claim 1, further comprising:

at least one unapertured pocket disposed thereon.

10. An absorbent article comprising:

a topsheet configured to contact skin of a user of the absorbent article;

a backsheet configured to contact a garment of the user of the absorbent article;

an absorbent core in between the topsheet and the backsheet; and a fluid distribution material in between the topsheet and the absorbent core, wherein at least one of the topsheet and the fluid distribution material comprises the formed film laminate of claim 1.

11. The absorbent article according to claim 10, wherein the topsheet is directly bonded to the fluid distribution material.

12. The absorbent article according to claim 11, wherein the topsheet is vacuum laminated to the fluid distribution material.

13. The absorbent article according to claim 11, wherein the topsheet comprises the formed film laminate.

14. The absorbent article according to claim 11, wherein the fluid distribution material comprises the formed film laminate.

* * * * *